(12) United States Patent
Henon et al.

(10) Patent No.: US 10,676,705 B2
(45) Date of Patent: Jun. 9, 2020

(54) AUTOMATED APPARATUS AND METHOD OF CELL CULTURE

(75) Inventors: Philippe Henon, Mulhouse (FR); Claire Saucourt, Mulhouse (FR); Patrick Gasse, Maurepas (FR); Alain Sundas, Fontenay-le-Fleury (FR); Pierre Sugranes, Conflans-Sainte-Honorine (FR); Amandine Verdier, Malakoff (FR); Frederic Demonchy, Elancourt (FR)

(73) Assignee: CELLPROTHERA, Mulhouse (FR)

( * ) Notice: Subject to any disclaimer, the term of this patent is extended or adjusted under 35 U.S.C. 154(b) by 751 days.

(21) Appl. No.: 13/492,356

(22) Filed: Jun. 8, 2012

(65) Prior Publication Data
US 2013/0244322 A1 Sep. 19, 2013

(30) Foreign Application Priority Data

Mar. 15, 2012 (EP) ..................................... 12305310

(51) Int. Cl.
*C12M 1/00* (2006.01)
*C12M 1/36* (2006.01)
(Continued)

(52) U.S. Cl.
CPC ............ *C12M 23/26* (2013.01); *C12M 23/14* (2013.01); *C12M 27/10* (2013.01); *C12M 27/16* (2013.01); *C12M 41/14* (2013.01); *C12M 41/48* (2013.01)

(58) Field of Classification Search
CPC ...... C12M 23/14; C12M 23/26; C12M 41/48; C12M 27/16; C12M 41/14; C12M 27/10;
(Continued)

(56) References Cited

U.S. PATENT DOCUMENTS 3,163,404 A * 12/1964 Kraft ....................... B01F 9/002
366/214
4,829,002 A 5/1989 Pattillo et al.
(Continued)

FOREIGN PATENT DOCUMENTS

DE 10 2006 022652 A1 11/2007
EP 1 932 904 6/2008
(Continued)

OTHER PUBLICATIONS

Extended European Search Report for European Patent Application No. 12305310.0 dated Aug. 2, 2012, 8 pages.
(Continued)

*Primary Examiner* — William H. Beisner
*Assistant Examiner* — Danielle B Henkel
(74) *Attorney, Agent, or Firm* — Alston & Bird LLP

(57) ABSTRACT

The invention provides an automated apparatus of cell culture having tanks of culture medium, of growth factors and of cells to be cultured, an incubator having a thermostated enclosure which houses a cell culture vessel, and control computer system. A supporting and agitation device of the culture vessel is provided in the enclosure, and the culture vessel is formed by a bag having at least one inlet port connected to the tanks and one outlet port connected devices for harvesting and storage of the cells after culture, these harvesting and storage devices and tanks being located outside the enclosure and being connected to the cell expansion bag ports by conduits which together with the cell expansion bag form a preassembled module passing through a wall of the enclosure.

26 Claims, 11 Drawing Sheets

(51) Int. Cl.
*C12M 3/04* (2006.01)
*C12M 3/06* (2006.01)

(58) Field of Classification Search
CPC ...... C12M 25/02; C12M 29/10; C12M 35/04; C12M 35/08; C07K 14/5403; C07K 14/5412; C07K 14/535; C12N 5/0641; C12N 5/0642; C12N 2502/1394; C12N 2501/14; C12N 2501/22; C12N 2501/23; C12N 2501/39; C12N 2502/99; C12N 2502/13; A61K 48/00
USPC ............ 435/286.5, 325, 305.1, 300.1, 289.1, 435/303.3, 297.1
See application file for complete search history.

(56) References Cited

U.S. PATENT DOCUMENTS

| | | | |
|---|---|---|---|
| 5,352,213 A | | 10/1994 | Woodard |
| 5,424,209 A * | | 6/1995 | Kearney ............... C12M 41/48 435/286.5 |
| 5,888,807 A * | | 3/1999 | Palsson .............. C07K 14/5403 435/289.1 |
| 2003/0064503 A1* | | 4/2003 | Abuljadayel .............. 435/285.1 |
| 2004/0110274 A1 | | 1/2004 | Manzo |
| 2007/0196911 A1* | | 8/2007 | Mambrini et al. ......... 435/297.5 |
| 2008/0118977 A1 | | 5/2008 | Henon |
| 2008/0220523 A1* | | 9/2008 | Antwiler ................ C12M 25/10 435/394 |
| 2011/0014689 A1* | | 1/2011 | Gandlur ................ C12M 23/14 435/289.1 |
| 2013/0316446 A1* | | 11/2013 | Andersson ............. C12M 23/14 435/305.1 |

FOREIGN PATENT DOCUMENTS

| | | |
|---|---|---|
| EP | 1 944 359 A1 | 7/2008 |
| EP | 1 978 089 A1 | 10/2008 |
| EP | 2 325 297 A2 | 5/2011 |
| SE | 1150154-1 * | 2/2011 |
| WO | WO-2000/073411 A1 | 12/2000 |
| WO | WO-2011/005773 A2 | 1/2011 |

OTHER PUBLICATIONS

International Search Report and Written Opinion of the International Searching Authority for International Patent Application No. PCT/EP2013/055244 dated Jun. 13, 2013, with English translation, 24 pages.

* cited by examiner

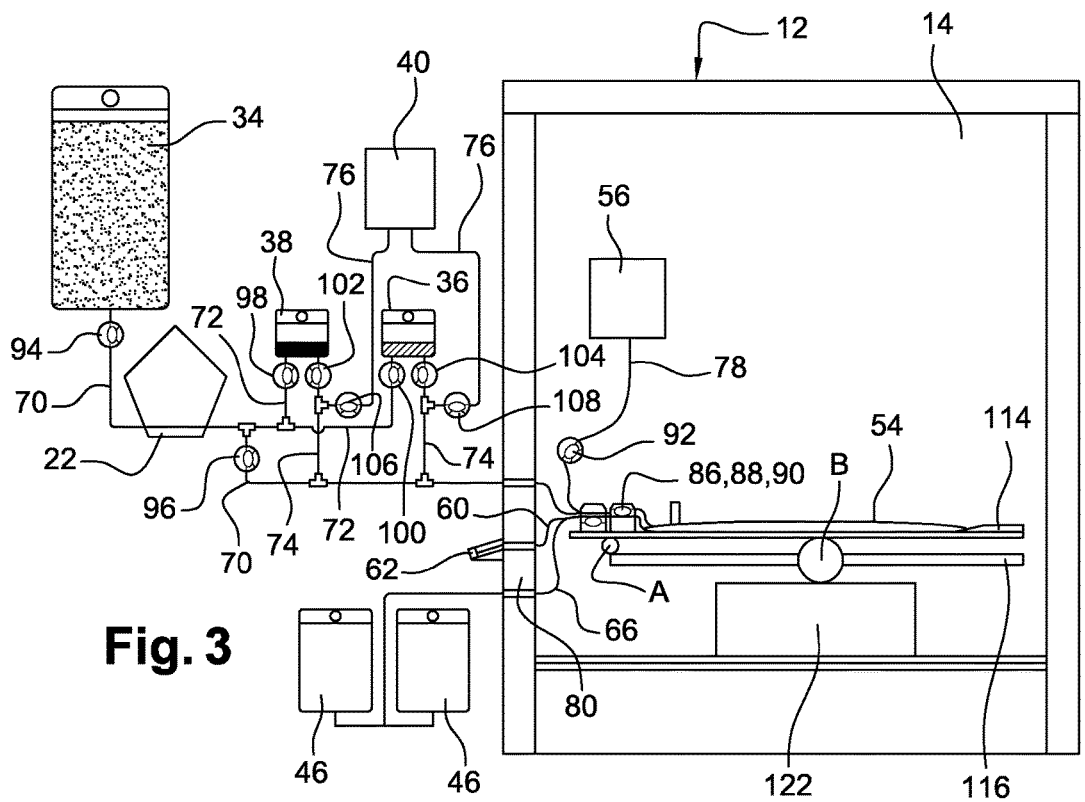
Fig. 3
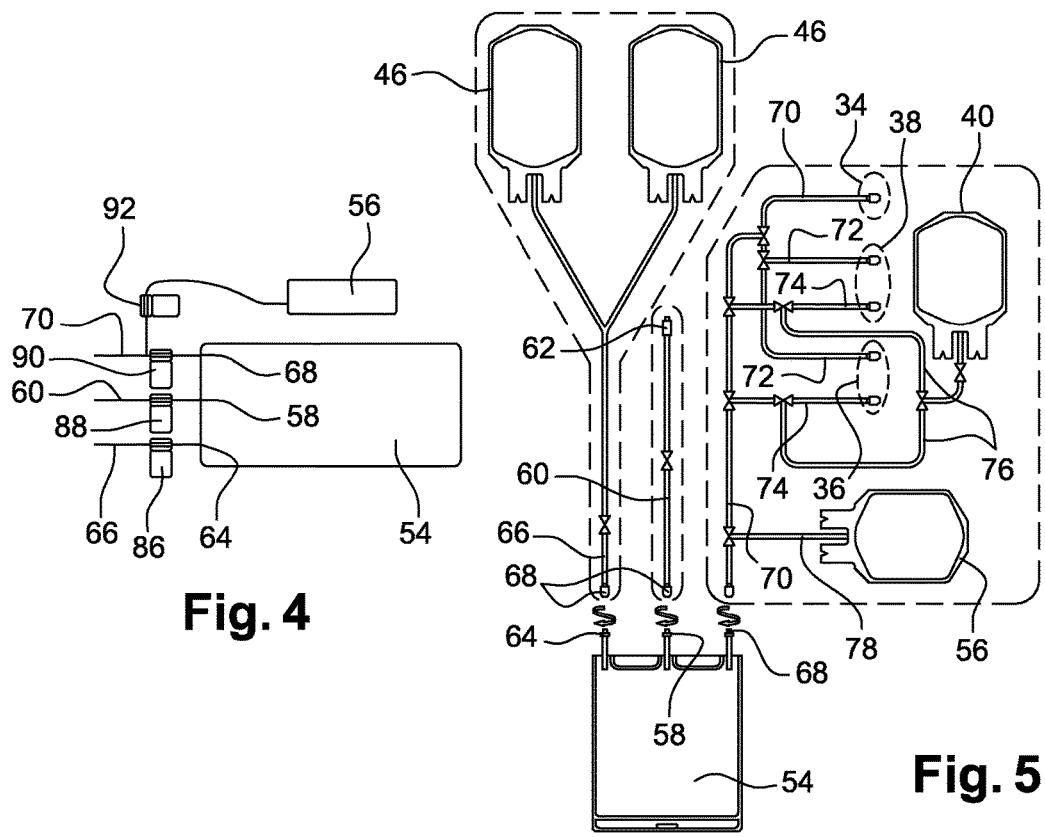
Fig. 4
Fig. 5

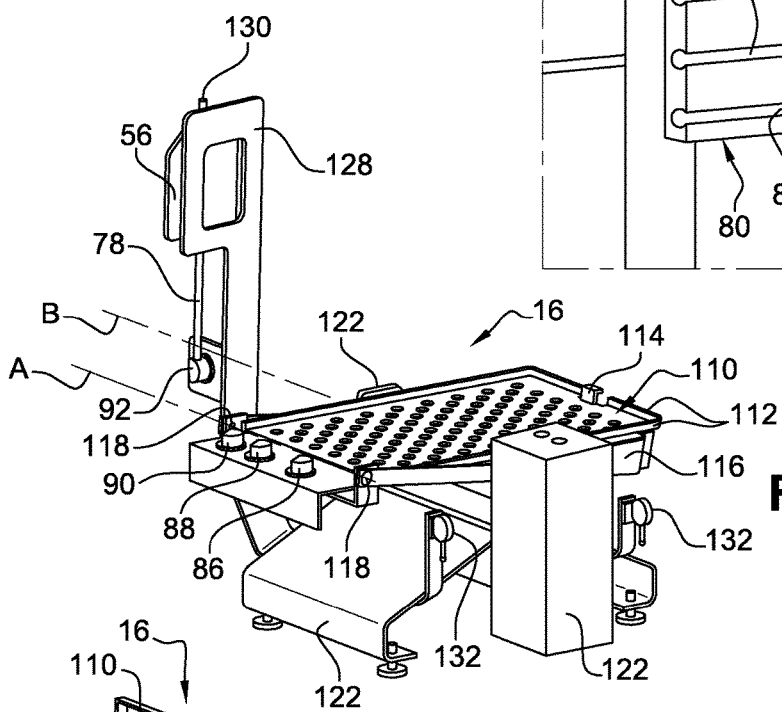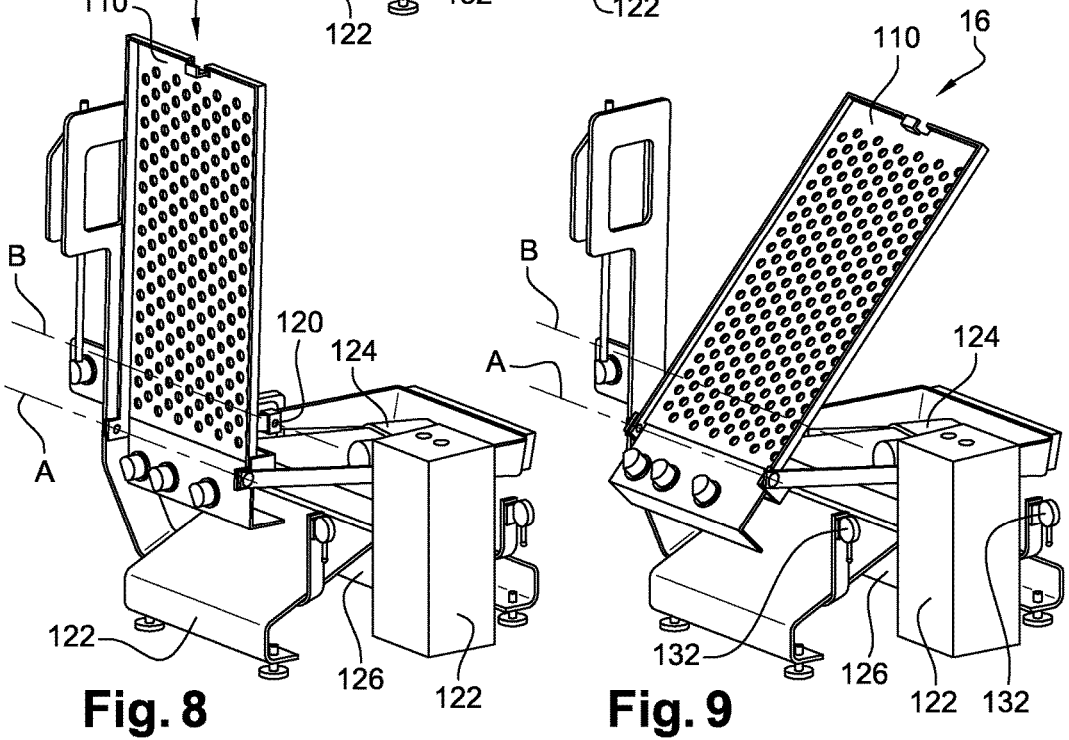

AUTOMATED APPARATUS AND METHOD OF CELL CULTURE

CROSS-REFERENCE TO RELATED APPLICATIONS

This application claims priority under 35 U.S.C. § 119 to European Patent Application No. 12305310.0 filed on Mar. 15, 2012, in the European Intellectual Property Office, the disclosure of which is hereby incorporated by reference in its entirety.

FIELD

The present invention relates to a cell culture automated apparatus particularly for the culture of stem cells (CD34+ type for example), and a method of cell culture using said automated apparatus.

BACKGROUND OF THE INVENTION

Among the fields involving cell culture, cell therapy is the least advanced in terms of industrialization. There is therefore a great need to find a technology capable of producing cells in sufficient quantity and in optimal conditions for these cells to be used for therapeutic applications.

Some cell therapy processes require culture or expansion of stem cells before reinjection into a patient, because the samples taken are sometimes insufficient to present a therapeutic effect. It is essential to ensure the integrity of the therapeutic properties of cells during cultivation. In the prior art, solutions for growing stem cells ex vivo are crafty, empirical and quite inefficient.

Moreover, the current technique does not allow producing stem cells in sufficient quantities for therapeutic applications. There is therefore a real need to develop a type of bioreactor with a compact geometry allowing the growth of cells in large quantities.

There are proposals using bioreactors for stem cell culture. However, the amplification phase is still a manual step and environmental conditions for cell culture (temperature, $CO_2$, etc. . . . ) are not monitored with high precision.

Existing examples of perfusion bioreactors with membranes, hollow fiber bioreactors, fluidized bed, and microbioreactors with continuous infusion of $O_2$, nutrient medium and growth factors are known.

Patent Application US-A1-2008/0118977 describes a treatment protocol for reconstructing a patient's heart after an infarct. The reconstruction is obtained by injecting into the heart of the patient specific stem cells (CD34+), isolated from a blood sample, expanded ex vivo and purified after culture.

SUMMARY OF THE INVENTION

The present invention is intended to provide a technology capable of culture, amplification or expansion of such cells, and also to bring significant improvements in terms of standardization, traceability and control of operations that are mostly done manually in the prior art.

The present invention therefore proposes an automated apparatus of cell culture, comprising tanks of culture medium, growth factors and cells to be cultured, an incubator with a thermostated enclosure in which is housed a container for cell culture or expansion, and a control computer system including means for entering and recording data intended to control the culture conditions in the enclosure and to manage valves for dispensing fluids in a predefined sequence, wherein it comprises a device for supporting and agitating the cell culture or expansion container which is controlled by said computer system and which is housed in said enclosure, and wherein said container is formed by a cell expansion bag having at least one inlet port connected to said tanks and one outlet port connected to means of harvesting and storage of the cells after culture, these harvesting and storage means and said tanks being located outside the enclosure and being connected to said ports of said cell expansion bag by conduits which form with said cell expansion bag a preassembled module placed in said enclosure and which pass through a wall of said enclosure so as to allow to feed the cell expansion bag with said culture medium, growth factors and cells to be cultured, and to harvest the contents of said cell expansion bag in the harvesting and storage means while maintaining the enclosure closed.

The main function of the automated apparatus according to the invention is to automate the steps of the biologic culture protocol and to control the environmental conditions (temperature control, $CO_2$ levels, etc.) of the cells cultured in the incubator in order to produce optimum yield of cell amplification. It also has the function of distribution of the culture medium, growth factors and cells to grow to a cell expansion bag (which may have a relatively large volume) in the incubator through operating means such as valves and pumps. The automated apparatus also ensures the agitation of the cell expansion bag and the transfer of cells after culture, from the cell expansion bag to the harvesting and storage means.

The automated apparatus according to the invention can thus be used to generate large quantities of cells such as stem cells, from cells taken from a patient. The bag in which cell culture is carried out may have a volume greater than 100 ml, 200 ml, 300 ml, 500 ml, which is for example approximately 650 ml or even more (1 L, 2 L, 3 L, etc.). The stem cell culture in a bag of this type can generate sufficient cells to perform cell therapy in a patient, as for example a patient who suffered a severe infarct, according to the biological protocol described in the application US-A1-2008/0118977.

The cell expansion bag preferably comprises liquid-tight and gas permeable flexible walls. It preferably has a good permeability to oxygen and carbon dioxide which allows a good aeration of the contents of the bag without opening it and therefore without risk of contamination of its content. In a particular embodiment of the bag, it includes the following permeability characteristics (in cc per day, at 37° C.): $O_2$ (gas)≈418, $CO_2$ (gas)≈966, $N_2$ (gas)≈157, and $H_2O$ (liquid) ≈0.05.

The cell expansion bag has preferably few or no affinity with chemical and biological products, especially with the cells to grow, and do not absorb such products. The bag is for example formed of a thin film of FEP copolymer (fluoro-ethylene-propylene). The bag can be equipped with different types of ports (modifiable interfaces) of which, for example, FEP fittings. They are assembled to the bag to minimize the risk of contamination.

The automated apparatus is designed to perform cell culture and includes all means and resources to achieve this culture, without the need for an operator to manipulate valves, replace bags or reservoirs, etc. Cell culture is performed according to a strict biological protocol fully managed by the computer system, which allows for example to operate the valves, the agitation device, and regulate the environmental conditions within the walls of the incubator. The operator can feed the computer system with data identifying the patient, collected cells and the nature and origin of different reservoirs or bags, so that all these data are saved and stored in the computer system. The invention thus allows implementing biological protocols with very good reproducibility and ensuring traceability and accurate control of protocols and used means.

Control and traceability of steps of the biological protocol may be carried out by the computer system and an appropriate graphic user interface (GUI), allowing for example to:
- define an automated culture method in which the specific parameters of biological culture protocol cannot be changed,
- ensure good security by limiting access to computer system data by the user's identification and the need for a password (in accordance with 21 CFR Part 11 FDA rules),
- allow recording events and various stages of the method, and
- edit reports (including test results of sampling and subsequent analysis of the characteristics of the graft, for example).

The cell expansion bag is housed in the enclosure and comprises at least two ports which are connected to ducts or conduits which pass through a wall of the incubator, and which are connected to reservoirs or tanks and to the storage means outside the enclosure. The cell expansion bag and the conduits form a preassembled single-use module, which is set up and replaced easily by the operator. At least a portion of the tanks contents located out of the enclosure is to be distributed in the cell expansion bag located in the enclosure, this content of which being intended after culture to be transferred to the harvesting and storage means outside the enclosure, all these fluid distribution operations being carried out while the walls of the incubator remain closed thanks to said conduits which pass through a wall of the incubator, and thus ensures optimal environmental conditions for the duration of the biological protocol and reduces the risk of contamination of the cells culture medium in the enclosure.

Advantageously, the cell expansion bag comprises at least one sampling outlet which is connected by a conduit to sampling means located outside the enclosure, said conduit passing through the wall of the enclosure and being part of said pre-assembled module. In this case, the cell expansion bag has three ports having different functions (feeding, harvesting and sampling) and which are connected to different conduits.

In one embodiment of the invention, the incubator includes a cabinet having an opening and a tight or sealed closure door, means for the passageway of said conduits being mounted on the peripheral edge of the opening and having grooves which are parallel to the conduits and into which the conduits are engaged, these grooves being intended to be covered by the door when in closed position. The conduits can be easily engaged in (and withdrawn from) these grooves by an operator when the door is open, by translating of the conduits in a direction perpendicular to the longitudinal axes of the grooves, which facilitates assembly of consumables.

The tanks of growth factors and of cells to be cultured are preferably formed by bags which are located above the inlet port of the cell expansion bag so that the content of each of the bags of growth factors and of cells to be cultured can flow by gravity to the cell expansion bag. This guarantees the integrity of the cells and growth factors during their transfer to the cell expansion bag. The use of a pump or any mechanical means to help circulation of cells and growth factors in the conduits may damage them.

The storage means may comprise one or two bags which are at least partially located below the outlet port of the cell expansion bag so that, after culturing, the content of the cell expansion bag can flow by gravity to the bags of the storage means. This also ensures the integrity of cells after culture, when harvesting.

The automated apparatus may include a peristaltic pump for controlling the supply of culture medium to the cell expansion bag and to both tanks of growth factors and of cells to be cultured for the rinsing of these tanks. The peristaltic pump has the advantage of not being in direct contact with the culture medium, thus avoiding risk of contamination of this medium.

The automated apparatus may further include two bags forming air trap, one of them being connected to the tanks of growth factors and of cells to be cultured r, and the other one being connected to the cell expansion bag, the air trap bags being intended to collect and store the air contained in the conduits, the cell expansion bag and/or the tanks.

Advantageously, the conduits are formed by flexible tubes, some of which passing through valves which are intended in a closed position, to pinch the tubes. Each tube is for example intended to be engaged in a groove of a valve in a simple manner by the operator, e.g., by translation in a direction substantially perpendicular to the longitudinal axis of the tube.

The supporting and agitation device may include a support plate or tray to support the cell expansion bag, which is mounted in rotation around a first horizontal axis and which is movable around said axis between a substantially horizontal position for cell culture and a substantially vertical position for harvesting of cells after culture. This position facilitates the harvesting of cells after culture, these cells flowing directly by gravity into the storage means referred to above.

The tray can be mounted in rotation around a second horizontal axis around which the tray is intended to oscillate for agitation and homogenization of the content of the cell expansion bag. The first and second axes of rotation of the plate are preferably parallel.

Preferably, the tray will carry valves for controlling the supply of the cell expansion bag, the harvesting of the content of the cell expansion bag, and the sampling of this bag.

The supporting and agitation device may further comprise a vertical arm having at its upper end means for attaching a bag forming an air trap connected to the cell expansion bag.

The harvesting and storage means are advantageously mounted in rotation around a horizontal axis and are movable around said axis between a substantially vertical position and a substantially horizontal position in which these means are located completely below the cell expansion bag. This ensures that the whole content of the cell expansion bag will be transferred by gravity into the storage means.

For example, in the particular case of culture of CD34+ stem cells, sterility required at the full conditioning chain of CD34+ cells requires the use and installation of consumables in the form of a single use cell culture kit.

The present invention also relates to a cell culture kit, preferably of single use (disposable) and sterile, for a cell culture automated apparatus, which comprises at least one cell expansion bag and flexible tubes connecting this bag to other bags or tanks, the tubes and the cell expansion bag being pre-assembled and the cell expansion bag comprising an inlet port, an outlet port and optionally a sampling outlet port.

The kit may further comprise all the necessary connecting devices required to connect the tubes to each other and to bags and/or tanks, as well as to the means connected to the third port of the cell expansion bag to allow cell sampling. All these elements can be part of the above mentioned preassembled module.

Advantageously, the inlet port of the cell expansion bag is connected by tubes to inlet and outlet ports of the bag of growth factors, and to inlet and outlet ports of the bag of cells to be cultured. The inlet port of the cell expansion bag is also intended to be connected to an outlet port of the culture medium bag.

The kit may further comprise two bags forming air trap one of which being connected to outlet ports of the bags of growth factors and of cells to be cultured, and the second one being connected to the inlet port of the cell expansion bag.

The kit may also comprise one or two harvesting bags of cells after culture, which are connected by tubes to the outlet port of the cell expansion bag.

As an example of embodiment of the invention, the growth factors and cells to be cultured bags and those forming an air trap have an internal volume of about 150 ml, the cell expansion bag has a theoretical volume of about 3000 ml and the two harvesting bags each has a volume of 600 ml. The distribution bag of the culture medium may have a volume of 1000 ml.

Advantageously, the kit forms a closed circuit which, once installed for a cell culture includes all the resources needed for this culture without requiring the addition of any product or operator intervention. This limits the risk of contamination of the kit and the culture medium.

The invention also relates to a supporting and agitation device for a cell culture automated apparatus, which comprises a support plate or tray for supporting a cell expansion bag, this tray carrying three valves and being mounted in rotation about a first horizontal axis for tilting the tray from a substantially horizontal position to a substantially vertical position, and about a second horizontal axis around which the tray is intended to oscillate for agitation and homogenization of the content of the cell expansion bag, the device also comprising monitored means for tilting the tray around said horizontal axes.

The device may comprise a vertical arm having at its upper end means for attaching a bag forming an air trap.

The invention also relates to an automated method of cell culture, by means of an automated apparatus as described above, which comprises the steps of:
a) feeding the cell expansion bag with cell culture medium, with growth factors, then with cells to be cultured while maintaining the walls of the incubator closed;
b) agitating the cell expansion bag in order to homogenize its content;
c) maintaining the cell expansion bag in incubation conditions for a period of several days for example, and
d) harvesting the content of the cell expansion bag in the harvesting and storage means while maintaining the walls of the enclosure closed.

The method according to the invention may comprise one or more of the following steps:
prior to step a), a step of installing the preassembled module by fitting the cell expansion bag on the support and agitation device, by mounting the conduits in the passageway means of the incubator and into the valves, and by connecting these conduits to tanks or bags, prior to step a), a step of evacuating the air contained in the conduits by passage of culture medium from the tank to the air trap bags;
after the supply of the cell expansion bag with growth factors in step a), a step of rinsing the growth factors tank by passing or flowing culture medium therein and then by flushing or draining its content to the cell expansion bag;
after the supply of the bag cell expansion with cells to be cultured in step a), a step of rinsing the tank of cells to be cultured by passing culture medium therein and then by draining its content to the cell expansion bag;
during step c), one or more steps of sampling the contents of the cell expansion bag, which are each preceded by a step of tilting the support tray from a horizontal position for culture onto an inclined position in which the sampling port is the lowest point of the bag;
prior to step c), a step of removing the culture medium bag, the growth factors bag and the bag containing the cells to be cultured by cutting and welding or pinching the conduit or tube connecting these tanks to the inlet port of the cell expansion bag;
before or during step d), a step of tilting the tray in a substantially vertical position so that the outlet port of the cell expansion bag represents the lowest point of the bag.

The invention also provides the use of an automated apparatus, a kit, or a device as described above for the culture of CD34+ stem cells or blood mononuclear cells, such as, for example lymphocytes. Stem cells can be issued from one or more sources such as umbilical cord blood, bone marrow and whole blood.

BRIEF DESCRIPTION OF THE DRAWINGS

The invention will be better understood and other details, advantages and features of the invention will become apparent upon reading the following non-limiting description given as an example and with reference to the accompanying drawings in which:

FIG. 3 is a very schematic view of the automated apparatus of FIGS. 1 and 2, without the computer system;

FIG. 4 is a very schematic view of components carried by an agitation device of the automated apparatus of FIGS. 1 and 2;

FIG. 5 is a schematic view of a cell culture kit according to the invention;

FIG. 6 is a schematic perspective view of passageway means for passing fluid conduits of the automated apparatus of FIGS. 1 and 2;

FIG. 7 is a schematic perspective view of the agitation device of the invention;

FIGS. 8 and 9 are schematic perspective views of the device of FIG. 7 and represent two different positions of inclination of the tray of the device;

DETAILED DESCRIPTION

Figure 1:
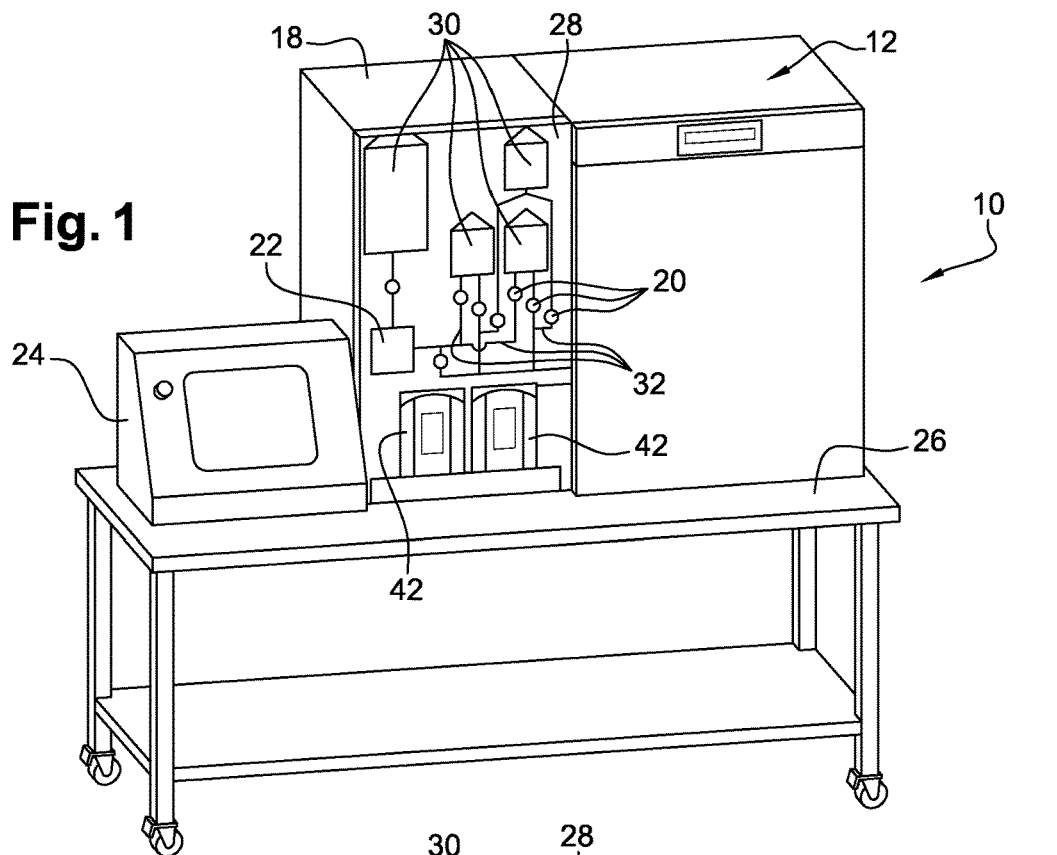
FIGS. 1 and 2 are schematic perspective views of the cell culture automated apparatus according to the invention, this automated apparatus including a cabinet defining an enclosure that is closed in FIG. 1 and open in FIG. 2.
Figure 2:
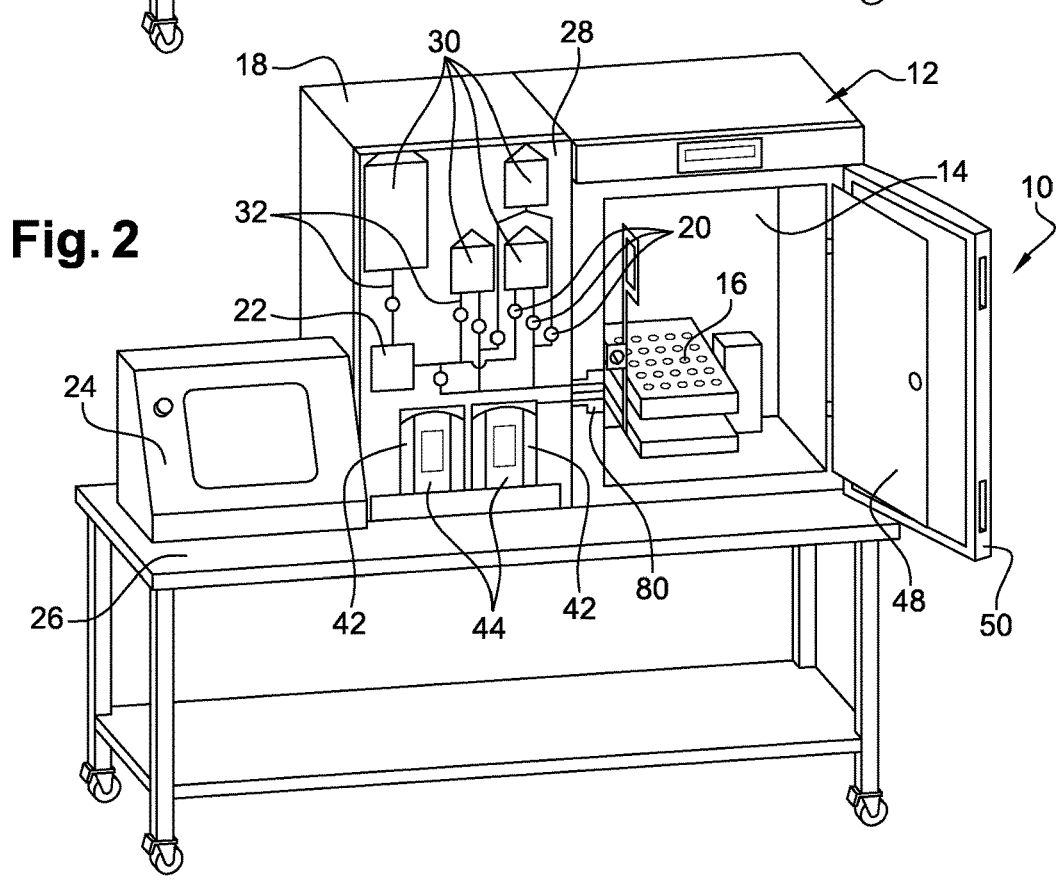

Referring first to FIGS. 1 and 2, which show an embodiment of the cell culture automated apparatus 10 according to the invention, this automated apparatus is particularly but not exclusively designed for cultivation of stem cells, for example according to the biological protocol US-A1-2008/0118977 described in the application which content is incorporated herein by reference.

In the example shown, the automated apparatus 10 essentially includes three elements:
- an incubator 12 with a thermostated enclosure 14 which houses a supporting and agitation device 16 of a cell expansion bag (not shown),
- a frame 18 to support bags (not shown) containing required media to culture cells, and bearing means (valves 20, pump 22, etc.) of distribution and regulation of fluid flow between the bags, and
- a computer system 24 connected to the incubator 12 and to the means 20, 22 for monitoring and controlling them and for entering and recording data and for managing the biological protocol.

In the example shown, the incubator 12, the frame 18 and the computer system 24 are placed one besides the other on a support 26 which is mounted on wheels, the frame 18 being located between the computer system 24 and the incubator 12.

Typically, the computer system 24 includes input and recording data, data processing means, display means, and means for transmitting signals for controlling and monitoring of the incubator 12 and of the means 20, 22 of the frame 18. Preferably, the computer system 24 includes a touch screen display and data entry facility.

To limit access to pre-recorded data of the computer system 24, multiple levels of security can be implemented. The manufacturer of the automated apparatus may have a right of access to maximum level, using a specific password, in order to access all information stored in the computer system 24, while an administrator and an operator with lower access levels will have access via specific passwords to certain information only.

The computer system 24 is preferably connected to a computer network via an Ethernet connection or Wi-Fi for example, so that the information of the computer system 24 can be accessed from a workstation on the network, remote from the automate 10, and that actions may possibly be required and controlled from that workstation.

The computer system 24 controls for example the opening and closing of valves 20, which are for example of on/off type, the setting of the flow rate of the pump 22, the heating control of the enclosure 14 of the incubator 12 (at a temperature of about 37° C. for example) and the feeding of the enclosure with gas such as $CO_2$ (at a rate of about 5% for example). The system 24 can ensure the regulation of other parameters if required within the enclosure 14, to define optimal environmental conditions for culturing the cells.

For better clarity, the connecting means of the computer system 24 to the means 18, 20 and to the incubator 12, the means for heating and supplying gas to the incubator 12, and the power supply means are not shown in the drawings.

The frame 18 has a shape similar to a parallelepiped and includes a front vertical face 28 on which are schematically drawn rectangles 30 representing the positions of biological media tanks, in the form of bags, as well as lines 32 representing the location of fluid(s) conduits between the bags.

The upper part of the front face 28 includes four rectangles 30 drawn to inform an operator about the nature of each of the bags to be positioned at these rectangles, these bags belonging to a consumables kit that will be described in further detail below.

A large first rectangle is drawn in the top left corner of the front face 28 of the frame 18 and represents the position of a bag containing a culture medium (bag referenced 34 in FIG. 3). Three rectangles 30 of smaller dimensions are drawn in the upper right corner of the face 28 and respectively represent the positions of a growth factors bag, of a bag comprising the cells to be cultured, and of a bag forming an air trap (which are respectively referenced 36, 38 and 40 in FIG. 3).

The middle portion of the front face 28 of the frame 18 includes mounting holes of said valves 20 and pump 22, each of these elements (valves and pump) being located on a line 32 representing a fluid conduit, which is formed by a flexible tube of the consumables kit.

The lower part of the front face 28 carries two coplanar plates 42 placed one besides the other. These plates 42 are pivotally mounted at their lower ends around a common horizontal axis extending parallel to the front face 28. The plates 42 are movable in rotation around this axis between an upright or vertical position (shown in FIGS. 1 and 2) in which they extend parallel to and at a short distance from the front face 28, and a horizontal position in which they can bear on the support 26.

Rectangles 44 are drawn on the front faces of the plates 42, when in vertical position. These rectangles 44 inform the operator about the nature of the bags to be carried by the plates 42. Bags of harvesting and storage of cells after culture (referenced 46 in FIG. 3) are designed to be carried by the plates 42.

The bags 34, 36, 38, 40 and 46 of the consumables kit are intended to be attached or fixed on the front face 28 of the frame 18 and on the plates 42 by suitable means (not shown).

The incubator 12 includes a cabinet defining the enclosure 14 and having an opening which can be sealed by two doors 48, 50 which are pivotally mounted on one side of the opening, for example the right side.

The inner door 48 is a glass door which, in closed position, will bear on a peripheral seal 52 of the opening of the cabinet, this seal 52 is visible in FIG. 6. The outer door 50 is insulated and has a peripheral seal for bearing on the peripheral edge of the opening of the cabinet.

The computer system 24 may be connected to sensors for detecting the position (open or closed) of each door 48, 50, and can control the locking of the doors in particular during the incubation and cell culture phases.

The enclosure 14 of the incubator 12 has an internal volume of about 200 L.

In the example shown in FIGS. 3 to 5, the consumables kit is for single use for cell culture and includes bags 34, 36, 38, 40 and 46, the tubes mentioned above, a cell expansion bag 54 and a second bag 56 to trap air, these bags 54, 56 being carried by the agitation device 16 which will be described in detail further, with reference to FIGS. 7-13.

The cell expansion bag 54 is best seen in FIGS. 4 and 5 and may have an internal volume greater than 500 ml, and for example of 650 ml. It includes three ports, a sampling outlet port 58 connected by a tube 60 to sampling means 62, an outlet port 64 connected by a tube 66 to the bags 46 for harvesting the cells after culture, and an inlet port 68 connected by tubes to the bags 34, 36, 38 and 56.

The inlet port 68 of the cell expansion bag 54 is connected by a tube 70 to an inlet port of the bag 34 of culture medium. The bags 36, 38 of growth factors and of the cells to be cultured each comprises an inlet port which is connected to one end of a tube 72 the other end of which being connected to the tube 70, and an outlet port which is connected to one end of a tube 74 the other end of which being connected to the tube 70 (downstream from the connection point(s) of the tube 72 to the tube 70). The bag 40 comprises two ports which are connected by tubes 76 to the tubes 74, and the bag 56 forming an air trap comprises a port connected by a tube 78 to the tube 70, in the vicinity of the inlet port 68 of the bag 54 (FIGS. 4 and 5).

The cell expansion bag 54 and the tubes 60, 66, 70, 72, 74, 76 and 78 are preferably pre-assembled and are supplied sterile. The bags 34, 36, 38, 40, 46 and 56 are also supplied sterile. The bags 40, 46 and 56 are supplied empty and can be preassembled with the cell expansion bag 54 to the tubes mentioned above. The bag 38 of the cells to grow is also provided empty and can be pre-assembled with tubes or connected to tubes during installation of the kit in the automated apparatus. The bag 38 may be filled with a medium containing the cells to be cultured before or after the installation of the kit in the automated apparatus. The bags 34 and 36 are preferably provided full respectively with culture medium and growth factors.

All connections of tubes and tubes to the bags as well as the means of sampling, are also preferably part of a preassembled module which is schematically shown in FIG. 5, the bags 34, 36 and 38 which are not necessarily part of this module being represented by dashed lines.

The bags 36, 38, 40 and 56 have a volume of about 150 ml, the bags 46 have a volume of about 600 ml, and the bag 34 of culture medium has a volume of about 1000 ml.

In the case where the automated apparatus 10 is used to grow CD34+ stem cells, the bag 38 includes such cells originating from a patient's sample and eventually isolated and purified, and growth factors of the bag 36 are cytokines.

The cell expansion bag 54 and the bag 56 forming the air trap are carried by the agitation device 16 and are housed in the enclosure 14 of the incubator 12 (FIG. 3). The other bags 34, 36, 38, 40 and 46 and the sampling means 62 are located outside of the enclosure 14.

The tubes 60, 66 and 70 connecting the cell expansion bag 54 to elements located outside the enclosure 14 pass through a component of the incubator which allows the sealing of the enclosure 14, this component being represented in FIGS. 3 and 6.

This component is a wall element formed by a block 80 of material (e.g., in plastic material) which is fixed on the peripheral edge of the opening of the cabinet of the incubator 12 and which comprises three passageway grooves 82 for the tubes 60, 66, 70 referred to above. These grooves 82 are substantially straight and are at a distance from each other. The block 80 has a rather planar form and extends in a vertical plane. It comprises a rear face bearing against the peripheral edge of the opening of the cabinet and a front face on which are formed the grooves 82, which have a rather horizontal orientation and extend over the entire transverse dimension of the block.

The grooves 82 have a rather circular section and have an internal diameter slightly greater than that of the tubes 60, 66, 70. These tubes are intended to be engaged in these grooves completely and optionally pass through cut-outs 84 of the peripheral seal 52 of the edge of the opening of the cabinet.

In the closed position of the enclosure 14, the peripheral edge of the inner door 48 is intended to bear on the seal 52 and to cover the parts of the tubes 60, 66, 70 extending in the cut-outs 84 of the seal 52, and the peripheral seal of the outer door 50 is intended to bear on the front face of the block and to cover grooves 82 and the portions of the tubes 60, 66, 70 extending in the grooves.

In the example shown, the lower groove of the block 80 forms a passage of the tube 66 connecting the cell expansion bag 54 to the harvesting bags 46, the median groove forms a passage for the tube 60 connecting the bag 54 to the sampling means 62, and the upper groove forms a passage for the tube 70 connecting the bag 54 to the bags 34, 36, 38 and 40.

As shown in FIG. 3, the tube 70 is engaged in the pump 22 in the vicinity of the bag 34 of the culture medium, this pump is a peristaltic pump to avoid contamination of the culture medium.

The above mentioned valves 20 are solenoid valves which are in the example shown, twelve in number, and referenced from 86 to 108 in FIG. 3.

The tubes 66, 60, 70 and 78 are respectively engaged in four valves 86, 88, 90 and 92 which are carried by the agitation device 16 (FIGS. 3 and 4).

The portion of the tube 70 located outside the enclosure 14 is engaged in two valves 94 and 96 at a distance from each other one of which 94 being located close to culture medium bag 34. The other valve 96 is located downstream from the connection of the tube 70 to the tube 72 and upstream from the connection of the tube 70 to the tube 74.

The tubes 72 connected to the inlet ports of the bags 36 and 38 are engaged in valves 98 and 100, respectively, and the tubes 74 are connected to the outlet ports of the bags 36 and 38 are engaged in valves 102 and 104, respectively.

The tubes 76 connected to the bag 40 forming an air trap are each engaged in a valve 106, 108.

The pump 22 and the valves preferably comprise a transverse groove for mounting a tube by translation in a direction perpendicular to the longitudinal axis of the tube or groove.

As it is schematically shown in FIG. 3 and visible in FIG. 2, the bags 34, 36, 38, 40 and 56 and the tubes 40, 72, 74, 76, 78 connecting these bags to the cell expansion bag 54 are all located above this bag 54 when the latter is placed horizontally. The bags 46, the sampling means 62 and the tubes 60, 66 connecting these elements to the cell expansion bag 54 are all located below said bag 54 when the latter is placed horizontally.

The bags 36, 38 and 56 are located substantially in a same horizontal plane which is located below a horizontal plane in which the bags 34 and 40 are located.

The consumables kit may be installed in the automated device according to the following manner. The doors 48, 50 of the incubator 12 are opened. The bags 34, 36, 38, 40 and 46 are fixed to the frame and the bag 56 is fixed to the arm of the agitation device 16. The bag 54 is disposed in a flat position onto the agitation device 16. The tube 70 is engaged in the valves 94, 96 and also in the pump 22, the tubes 72 are engaged in the valves 98, 100, the tubes 74 are engaged in the valves 102, 104 and the tubes 76 are engaged in the valves 16, 108. The tubes 66, 66, 70 and 78 are engaged respectively in the valves 86, 88, 90 and 92 carried by the device 16, and then the tubes 66, 60 and 70 are engaged respectively in the grooves 82 of the block 80. The tubes are connected to the bags which are not already preassembled to the tubes, and then the doors 48, 50 of the incubator 12 are closed.

The following refers now to FIGS. 7 to 13, which show an embodiment of the agitation device 16 according to the invention.

Figure 10:
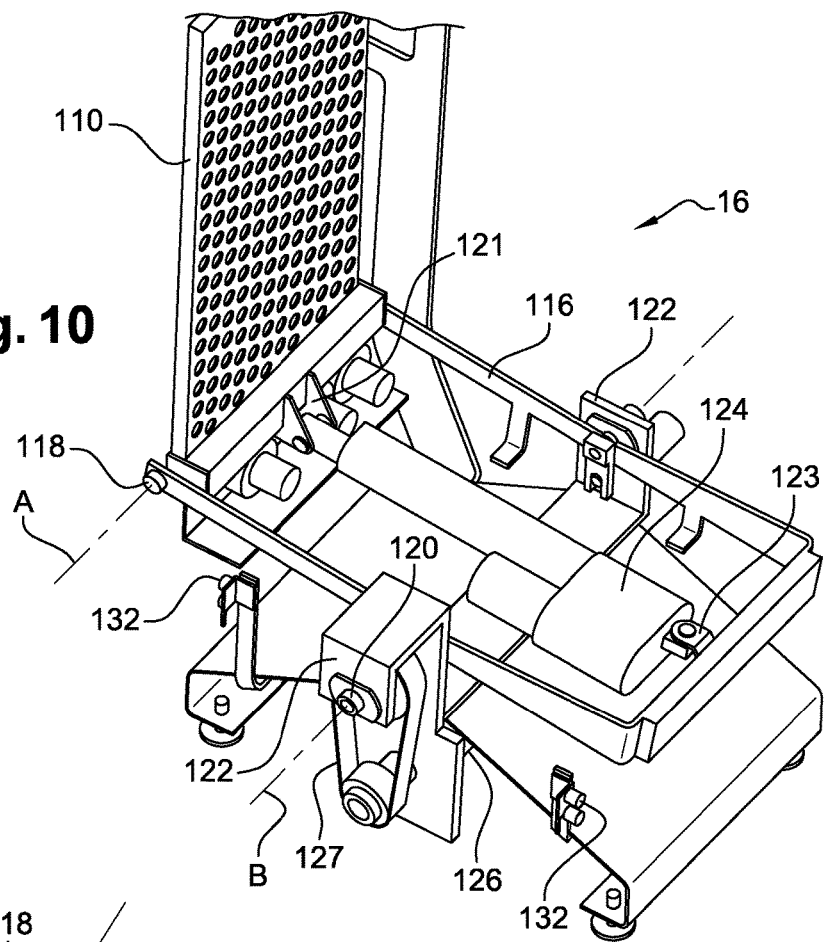
FIG. 10 is another schematic perspective view of the agitation device of FIG. 7, with partial cutaway of the cowling of the device.
Figure 11:
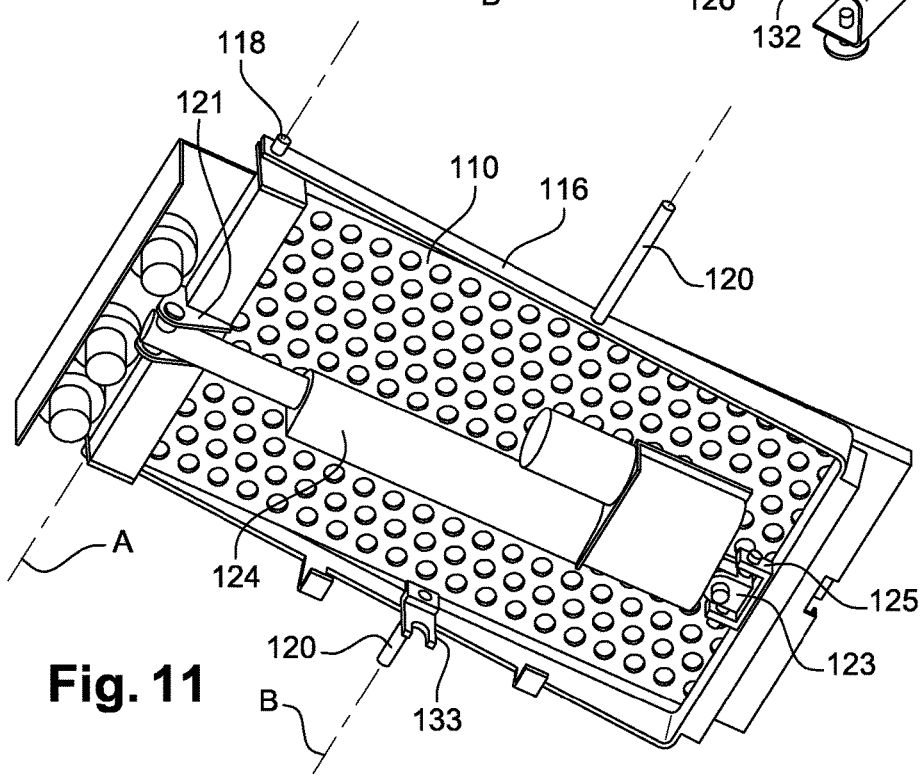
FIG. 11 is a schematic perspective view of the tray and controlled means for tilting the tray of the device of FIG. 7, seen from below.

The agitation device 16 comprises a plate or tray 110 for supporting the cell expansion bag 54 (not shown in FIGS. 7 to 13), this tray being mounted to be movable in rotation about a first horizontal axis A for moving the tray from a first substantially horizontal position shown in FIGS. 7 and 11 to a substantially vertical position shown in FIGS. 8 and 10 (the tray 110 being suitable to adopt any position between these extreme positions, such as a position shown in FIG. 9 in which it is inclined of about 45° with respect to a horizontal plane), and about a second horizontal axis B around which the plate or tray 110 is designed to oscillate (over an approximate angular range of +/−8°) to agitate and homogenize the content of the cell expansion bag.

The tray 110 has a rectangular shape which dimensions are slightly greater than those of the cell expansion bag 54 (approximately 40 cm in length and 22 cm wide), which is intended to be placed flat on the tray. The tray 110 includes peripheral retaining edges 112 of the bag and is perforated so that the face of the bag 54 pressed against the plate can be directly exposed at least in part to environmental conditions prevailing in the enclosure 14 of the incubator 12.

The tray 110 includes at one of its ends, corresponding to one of the short sides of the tray, a hook 114 to fix the cell expansion bag 54; said hook is intended to represent the highest point of the device 16 when the tray is in an upright or vertical position (FIG. 8). The tray 110 includes at the opposite end of the hook 114 three holes for mounting the valves 86, 88, 90 referred to above.

The device 16 comprises a U-shaped part 116 the free ends of the two lateral branches of which being articulated on pivots 118 fixed to the side edges of the end of the tray 110 carrying the valves 86, 88, 90. These pivots 118 are aligned and define the first axis of rotation of the tray 110 referred to above.

The branches of the U-shaped part 116 carry rather in their middle, pivots 120 which are articulated on a frame 122 of the device 16, these pivots 120 being aligned and define the second axis B referred to above of rotation of the plate 110.

When the tray 110 is in a rather horizontal position (FIG. 7), the U-shaped part 116 extends along three sides of the tray (along the longer sides and the short side with the hook 114).

The displacement of the tray 110 around the axis A is provided by a jack 124 which is mounted between the arms of the U-shaped part 116, the jack cylinder being attached to the middle part of this part 116 and the jack piston rod being fixed to the end of the tray carrying the valves 86, 88 and 90.

As it can be seen in FIGS. 10 and 11, the piston rod of the jack 124 is hinged on an axis carried by a clevis 121 fixed on the end of the tray 110 carrying the valves, this axis being substantially horizontal. The cylinder of the jack 124 is articulated on a rather vertical axis carried by a first clevis 123 which is itself articulated on a rather horizontal axis carried by a second clevis 125, the second clevis 125 being fixed to the middle portion of the part 116, substantially in a middle portion.

When the piston rod of the jack 124 is in its extended position, the tray 110 is in its rather horizontal position shown in FIGS. 7 and 11. When the piston rod of the jack 124 is in fully retracted position, the tray 110 is in its rather vertical position shown in FIGS. 8 and 10. In the case of FIG. 9, the piston rod of the jack 124 is partially retracted or output.

The displacement of the tray 110 around the axis B is provided by an electric motor 126 whose output shaft drives through a belt 127 a wheel intended to drive one of the pivots 120 carried by the U-shaped part 116 (FIG. 10). The motor 126 is fixed to the chassis 122 of the device by appropriate means.

Figure 12:
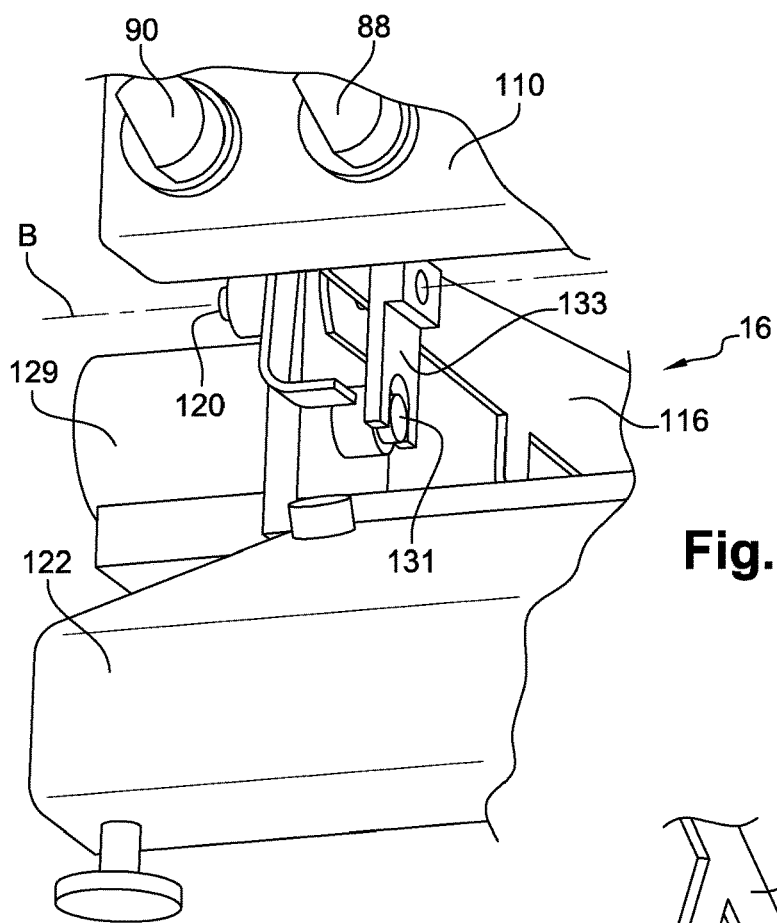
FIGS. 12 and 13 are schematic perspective views of a controlled locking system of rotation of the tray of the device shown in FIG. 7, the locking system being active in FIG. 11 and inactive in FIG. 12.
Figure 13:
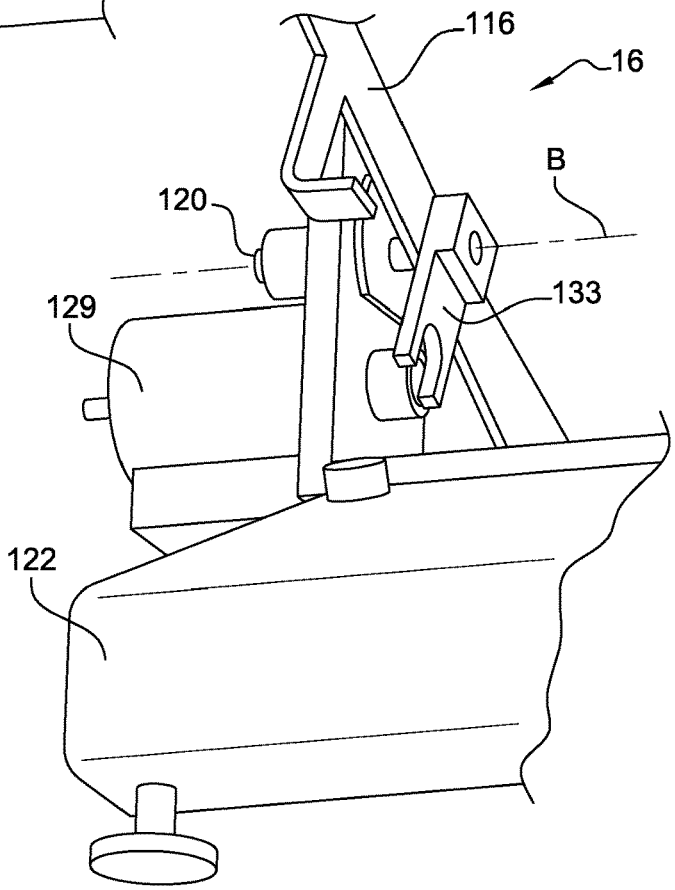

As shown in FIGS. 12 and 13, the chassis 122 of the agitation device 16 carries a system 129 for locking the rotation of the tray 110 around the axis B, the system 129 including a retractable finger 131 which cooperates with an element 133 carried by the U-shaped part 116 to block the tray.

The finger 131 is movable from an extended position shown in FIG. 12 to a retracted position shown in FIG. 13, the displacement of this finger being controlled by the computer system 24.

The element 133 carried by the part U-shaped 116 has an elongated shape and comprises a first end fastened to one of the pivots 120 and a second end with a notch in which the finger 131 is intended to be engaged in order to block rotation of the tray 110 around the axis B. When the finger 131 is deployed (FIG. 12), the side faces of the notch of the element 133 may abut on the finger thereby preventing any rotation of the tray around the axis B. When the finger is in the retracted position (FIG. 13), the U-shaped part 116 and the tray 110 can be moved in rotation around the axis B.

The blocking of the rotation of the tray 110 around the axis B can be activated by the computer system 24 when the tray is moved around the axis A to an inclined or vertical position, for sampling or harvesting of the cells of the cell expansion bag 54, to prevent the tray from moving around the axis B due to the force exerted on one side of the tray by the weight of the cell expansion bag.

The agitation device 16 also comprises a vertical arm 128 for fixing the above mentioned valve 92 and for attaching the bag 56 forming an air trap. The valve 92 is located substantially at a mid-height of the arm 128 and the upper end of the arm comprises a hook 130 to hang the bag 56 (FIGS. 7-9).

The device 16 further comprises sensors 132 of position of the plate 110 around the axes A and/or B, which are carried by the chassis 122.

Figure 14:
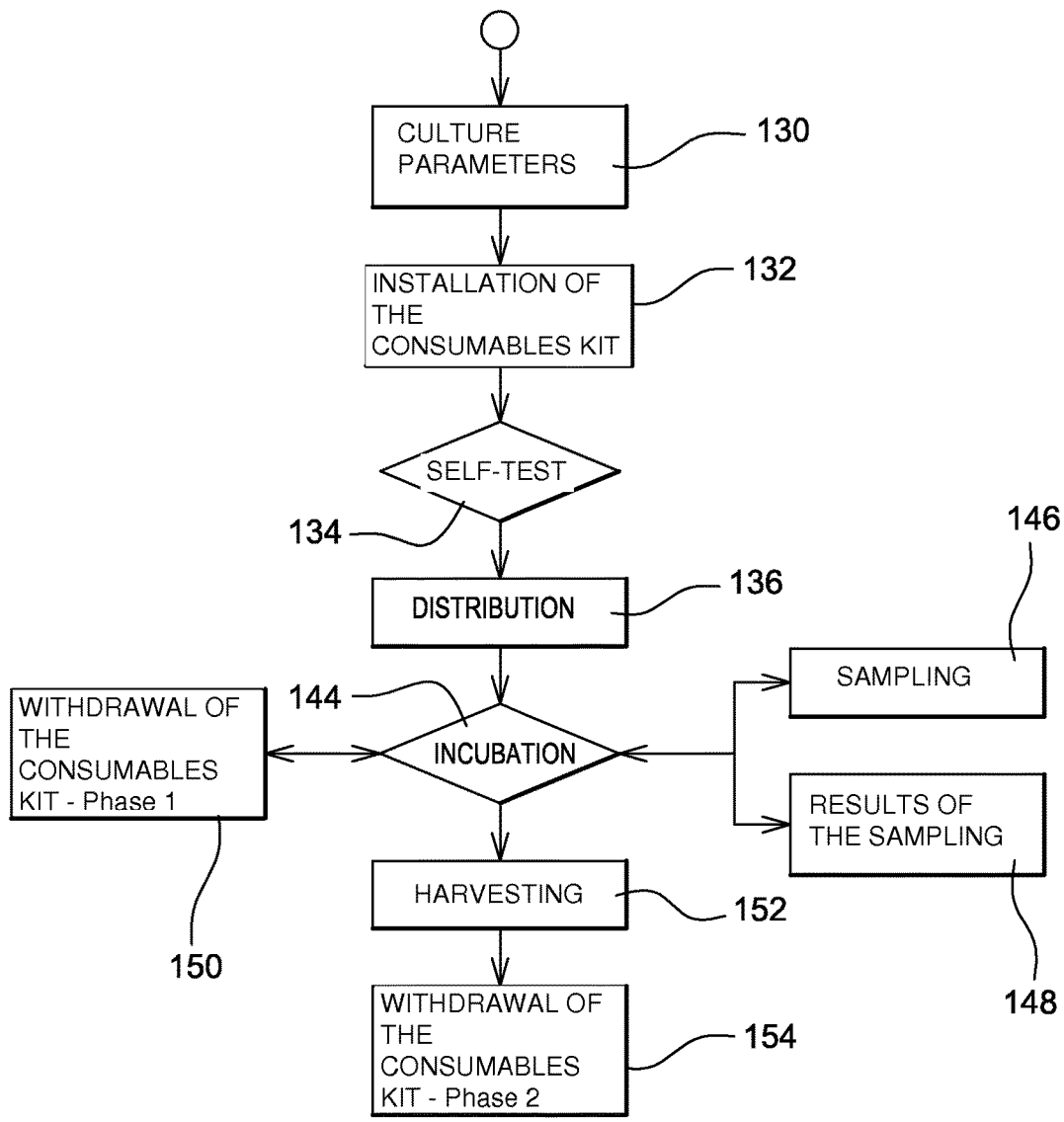
FIG. 14 is a flowchart showing steps of a cell culture method according to the invention.

FIG. 14 is a flowchart showing steps of the method according to the invention.

A first step 130 of the method is to record and enter culture parameters which are specific to the biological protocol, by using the computer system 24. The input is performed by an operator, the entered parameters being for example patient identification, identification of the consumables kit, the volume of the cell expansion bag 54, etc. To facilitate the input of these parameters, the computer system 24 can be equipped with a barcode reader; the consumables kit may include a barcode directly informing the computer system 24 with the number and nature of the kit as well as the volume of each bag.

The method includes a second installation step 132 of consumables kit to the automated apparatus 10, as described in the foregoing. This installation can be guided and supervised by the computer system 24. Installation can be done in several sub-steps, the computer system 24 showing installation instructions to the operator by indicating to validate or invalidate the creation of a sub-step and the transition to a next sub-step. These sub-steps are for example:

placing the different bags on the frame 18 and into the enclosure 14 of the incubator 12, placing the tubes 70 of the bag 34 of the culture medium in the valves 94, 96 (the computer system 24 controls the opening of the valves 94, 96 which are then closed when the operator has validated this sub-step)

placing the tubes 72, 74, 76 of the bag 36 of growth factors and the bag 40 forming an air trap in the valves 98, 102 and 106 (the computer system 24 controls the opening of these valves which are then closed when the operator has validated this sub-step)

placing the tubes 72, 74, 76 of bag 38 of cells to grow and the bag 40 forming an air trap in the valves 100, 104 and 108 (the computer system 24 controls the opening of these valves which are then closed when the operator has validated this sub-step)

placing the tube 78 of the bag 56 forming an air trap in the valve 92 (the computer system 24 controls the opening of this valve which is then closed when the operator has validated this sub-step), and placing the tubes 70, 60, 66, one after the other, in the valves 90, 88 and 86 (the computer system 24 controls the opening of each of these valves, one after the other, which are then closed when the operator has validated each sub-step).

The method of the invention comprises a third step 134 of test called "self-test" in which the computer system 24 controls the proper functioning of the valves and the means (jack 124 and motor 126) for tilting the tray 110 of the agitation device 16. The operation of the incubator 12 can be implicitly controlled at the start of the biological protocol, which can only be initiated if for example, the temperature and $CO_2$ levels, in the enclosure 14 are stabilized at incubation set points.

The method according to the invention comprises a further stage 136 of distribution of fluids, which comprises several sub-steps shown in the diagrams in FIGS. 15 to 19.

Figure 15:
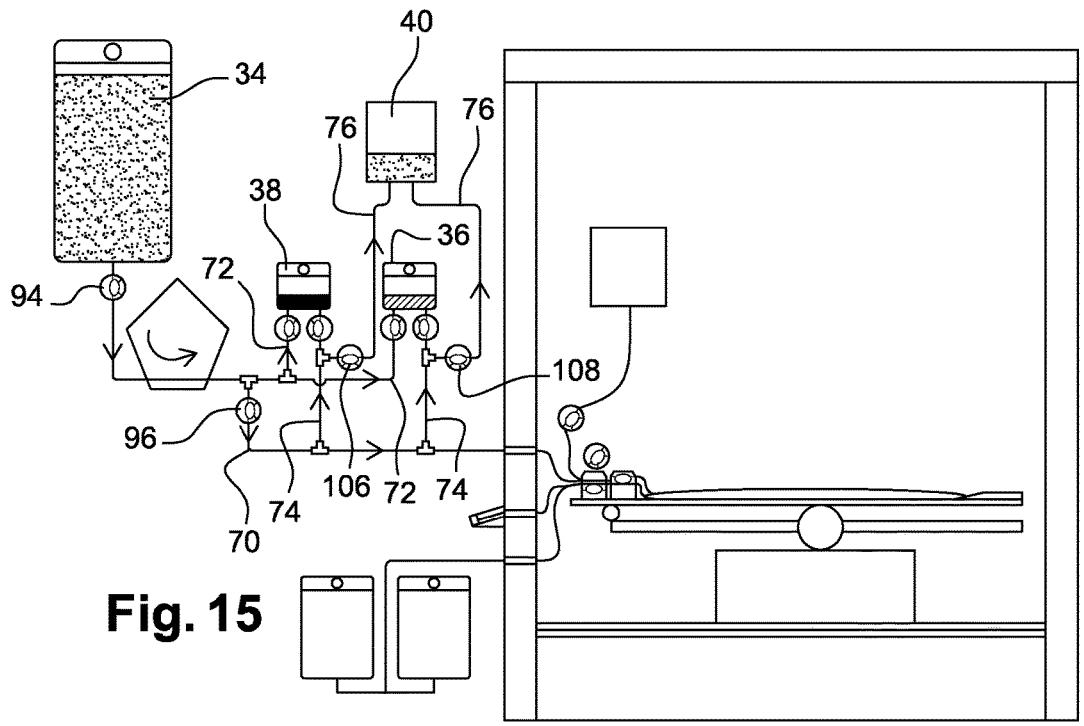
FIGS. 15 to 24 are views corresponding to FIG. 3 and representing steps of the method according to the invention.

The first sub-step of distribution step 136 is shown in FIG. 15 and consists in evacuating the air contained in the tubes 70, 72, 74. For this, the valves 94, 96, 106 and 108 are open and the pump 22 is set on by the computer system 24 so that the culture medium flows from the bag 34 in the tubes 70, 72, 74 up to the bag 40 forming an air trap. The tubes 70, 72, 74 are then filled up with culture medium and the bag 40 is at least partially filled with culture medium. The pump 22 is set at a predetermined flow rate and operates for a predetermined time, at the end of which the pump is stopped and the valves 94, 96, 106 and 108 are closed.

Figure 16:
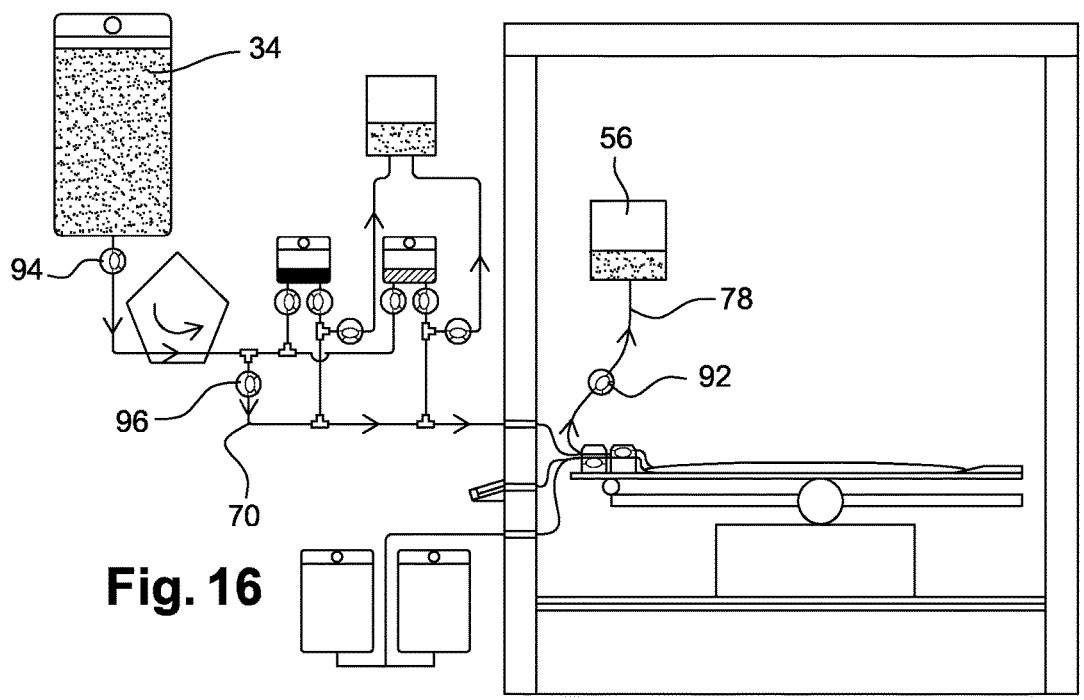

The second sub-step of the distribution step 136 is shown in FIG. 16 and consists in evacuating the air contained in the tubes 70 and 78. For this, the valves 94, 96 and 92 are open and the pump 22 is set on by the computer system 24 so that the culture medium flows from the bag 34 in the tubes 70, 78 to the bag 56 forming an air trap. The tube 78 is then filled with culture medium and the bag 56 is at least partially filled with culture medium. The pump 22 is set at a predetermined flow rate and operates for a predetermined time, at the end of which the pump is stopped and the valves 94, 96 and 92 are closed.

Figure 17:
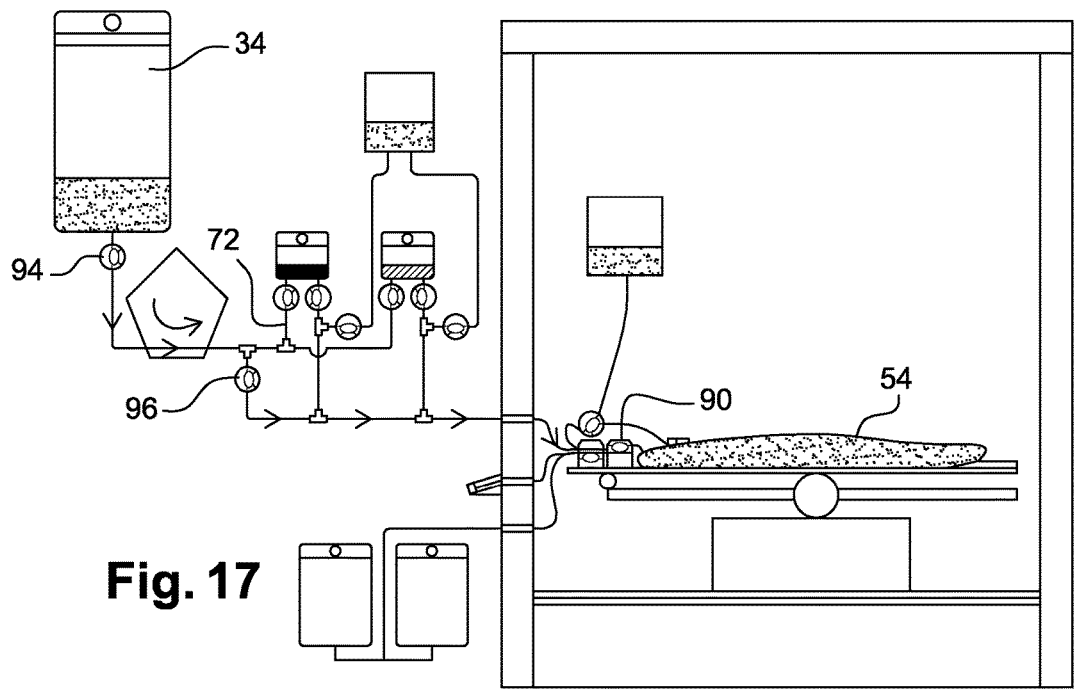

The third sub-step of the distribution step 136 is shown in FIG. 17 and consists in feeding the cell expansion bag 54 with culture medium. The valves 94, 96 and 90 are open and the pump 22 is set on by the computer system 24 so that the culture medium flows from the bag 34 to the bag 54. The bag 54 is then filled with culture medium. The pump 22 is set at a predetermined flow rate and operates for a predetermined time within the parameters of biological protocol specifying the volume of culture medium for distribution to the bag 54 as well as its feeding flow rate. The pump 22 is then stopped and the valves 94, 96, 90 are closed.

Figure 18:
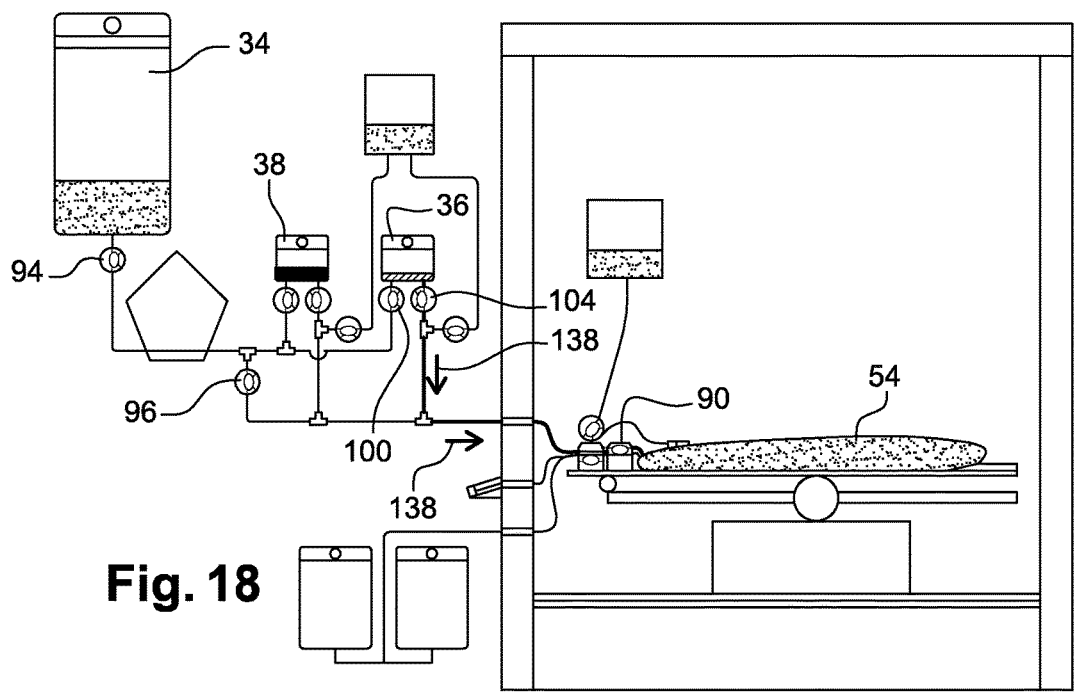

The fourth sub-step of the distribution step 136 is shown in FIG. 18 and consists in feeding the cell expansion bag 54 with growth factors and then rinsing the bag 36 of growth factors with culture medium and flowing the content of the bag 36 to the cell expansion bag 54. As a first step, the valves 104 and 90 are open, so as to allow the medium containing growth factors to flow by gravity from the bag 36 to the bag 54 by circulation in the tubes 74 and 70 (arrows 138). The bag 54 is filled with growth factors. The valves 104 and 90 are open for a predetermined time depending on the volume of medium containing growth factors to be distributed to the bag 54. After this period, the valves 104 and 90 are closed. The valves 94 and 100 are then open and the pump 22 is set on (at a predetermined flow rate and duration) to feed the bag 36 with culture medium for rinsing. The valves 94 and 100 are closed and the valves 104 and 90 are open again to let the rinsing product contained in the bag 36 to flow by gravity to the cell expansion bag 54. The valves 104 and 90 are open for a predetermined time depending on the volume of rinsing product to be dispensed to the bag 54. After this period, the valves 104 and 90 are closed. These steps to rinse the bag 36 and to drain the rinsing product into the cell expansion bag 54 can be repeated one or several times according to the parameters of the biological protocol, so that for example the totality of the growth factors contained originally in the bag 36 are distributed to the bag 54.

Figure 19:
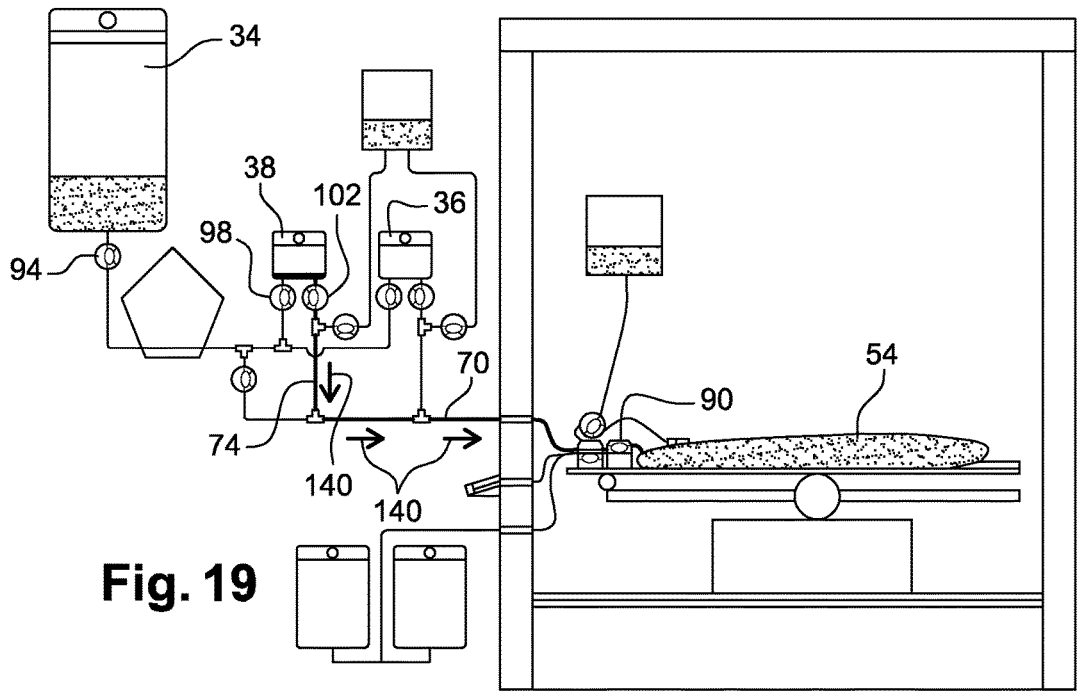

The fifth sub-step of the distribution step 136 is shown in FIG. 19 and consists in feeding the cell expansion bag 54 with cells to be cultured and then in rinsing the bag 38 containing the cells with culture medium and draining the content of the bag 38 to the cell expansion bag 54, in a manner similar to that performed at the fourth sub-step. At a first step, the valves 102 and 90 are open, so that the medium containing the cells to be cultured flows by gravity from bag 38 to bag 54 circulating in tubes 74 and 70 (arrows 140). The bag 54 is filled with cells to grow. The valves 102 and 90 are then closed and the valves 94 and 98 are open and the pump 22 is operated (at a predetermined flow rate and duration) to supply the bag 38 with culture medium for rinsing it. The valves 94 and 98 are closed and the valves 102 and 90 are open again to let the rinsing product contained in the bag 38 to flow by gravity to the cell expansion bag 54. The valves 102 and 90 are then closed. These phases to rinse the bag 38 and to drain the rinsing product to the cell expansion bag 54 can be repeated one or several times according to the parameters of the biological protocol, for example in order that all the cells to be cultured originally contained in the bag 36 are distributed to the bag 54.

Figure 20:
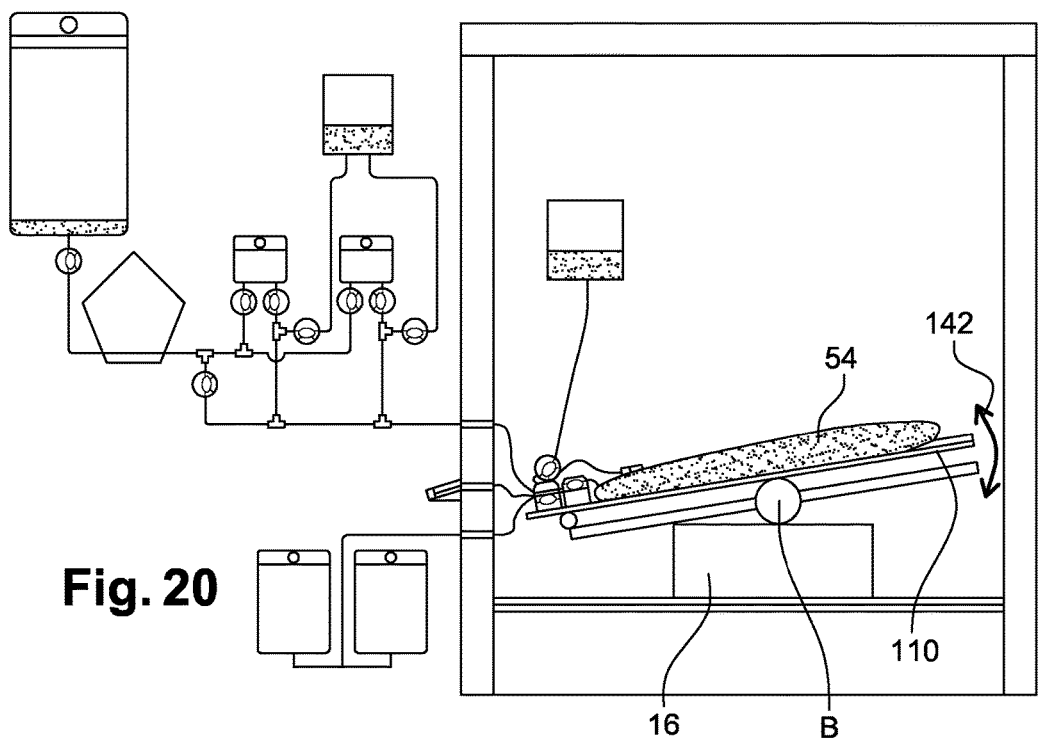

The step 136 of the distribution method can be followed by the homogenization of the content of the cell expansion bag 54, which is schematically shown in FIG. 20. At this step, the computer system 24 controls the agitation device 16 so that the tray 110 oscillates around the axis B, as explained in the foregoing (arrows 142). The amplitude, frequency, duration and timing (rest, agitation, rest, etc. . . . ) of these oscillations are determined by the parameters of the biological protocol.

The method of the invention then includes an incubation step 144 which may last several days for example ten days. Periodically, depending on the protocol parameters, the contents of the cell expansion bag 54 can be homogenized, moved by rotation of the tray around the axis B as explained above. This homogenization (periods, frequency, and amplitude) is determined by the protocol parameters independently of the homogenization step following the distribution step 136.

Figure 22:
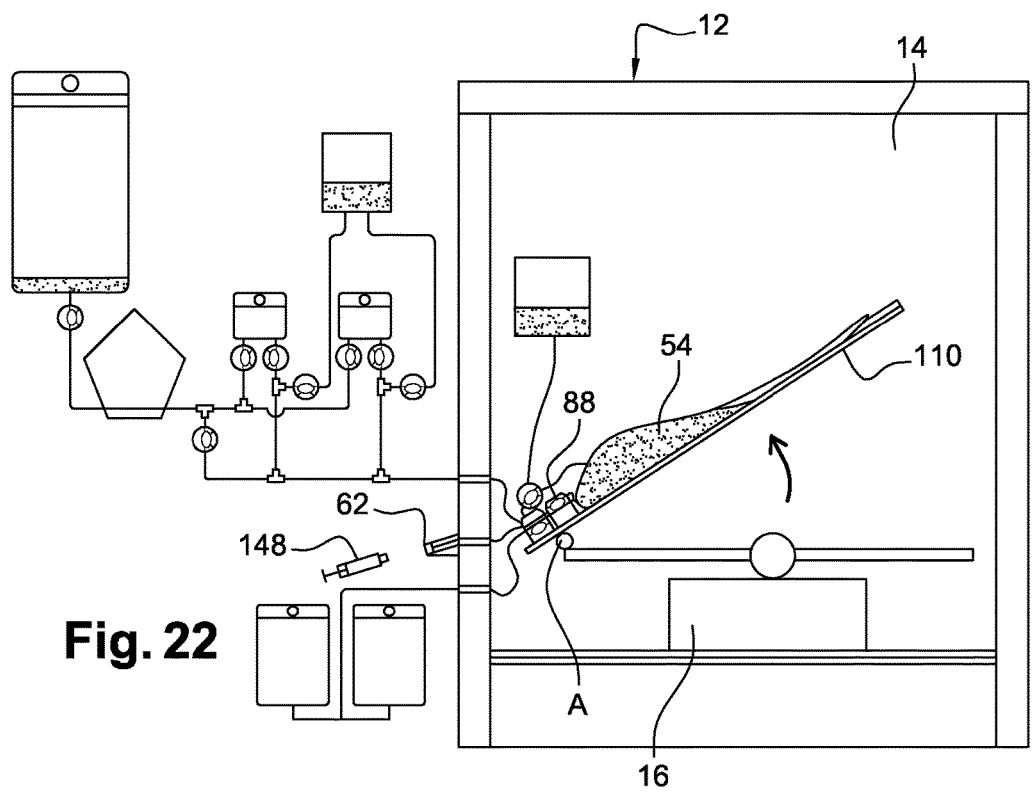

During the incubation step 144, the operator can perform one or more sampling 146 from the cell expansion bag 54 (FIGS. 14 and 22). Some of these samples may be imposed by the computer system. Three samples can be required for example and can be performed immediately after the distribution step, three days after the start of the incubation step 144, and seven days after the beginning of this step 144. Other samplings may be made on demand by the operator; the computer system can propose the operator to perform these voluntary samples.

When the operator confirms to the computer system 24 that she/he is ready to take a sample, the computer system operates the jack 124 so that the tray 110 of the agitation device 16 rotates around the axis A to an inclined position, for example 45°, with respect to a horizontal plane, as schematically shown in FIGS. 9 and 22. The computer system 24 can then detect the correct position of the tray 110 via the sensors of the device 16.

The computer system 24 controls the opening of the valve 88 so that a portion of the content of the cell expansion bag 54 flows by gravity from the bag 54 in the tube 60 to the sampling means 62 located outside the enclosure 14 of the incubator 12. The operator can take a sample from the cell expansion bag 54 using a syringe 148 equipped with a "Luer lock" type connection which is engaged in the sampling means 62. After sampling, the valve 88 is closed and the tray 110 of the agitation device 16 is returned to a substantially horizontal position.

The operator can then carry out analyzes of the sample; results 148 of these analyzes can be entered and stored in the computer system 24 by the operator.

Figure 21:
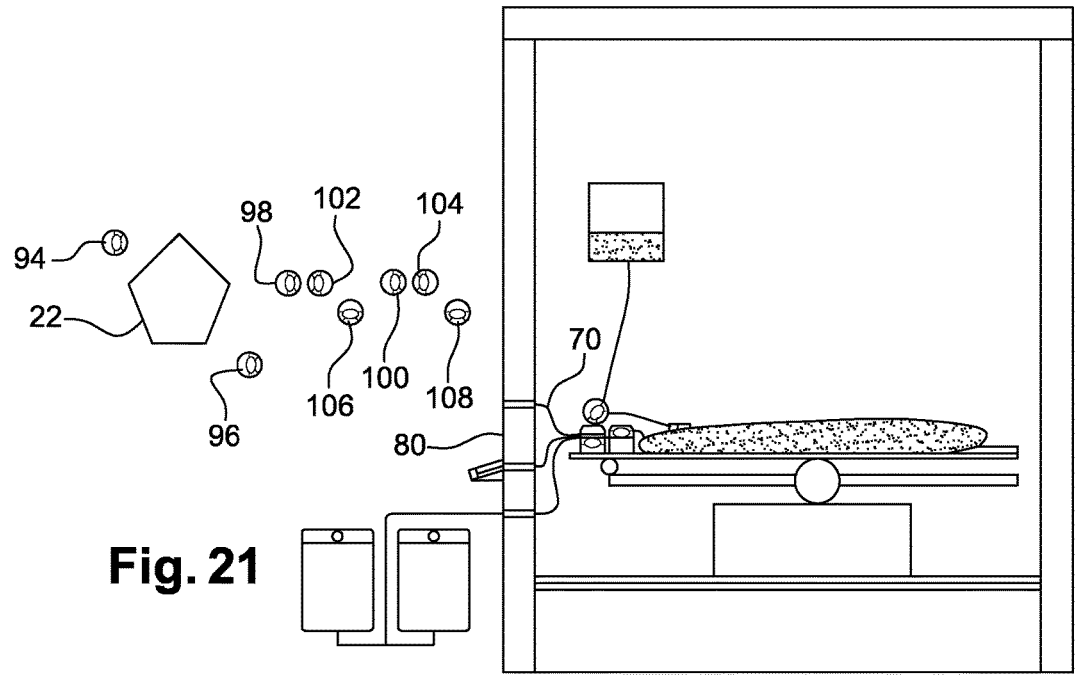

During the incubation step 144, the operator can also remove a portion of the consumables kit (first withdrawal phase 150 of the consumables—FIGS. 14 and 21). The components of the consumables kit which can be removed are all the bags (34, 36, 38, and 40) and tubes (72, 74 and 76) connected to the tube 70. For this, the operator must cut the tube 70 upstream of the crossing of above mentioned block 80 and must in the same time weld or pinch off the free end of the tube 70 remaining in the chamber 14 of the incubator 12, to avoid contamination of the cell expansion bag. This operation can be performed by the operator by means of appropriate cutting pliers or clippers sealing the end of the tube during cutting. The valves 94-108 are then opened to allow removal by the operator of the tubes 70, 72, 74, 76 from these valves as well as the pump 22 (FIG. 21). Once the operator has confirmed the removal of these elements to the computer system 24, the latter controls the closing of the valves 94 to 108.

Figure 23:
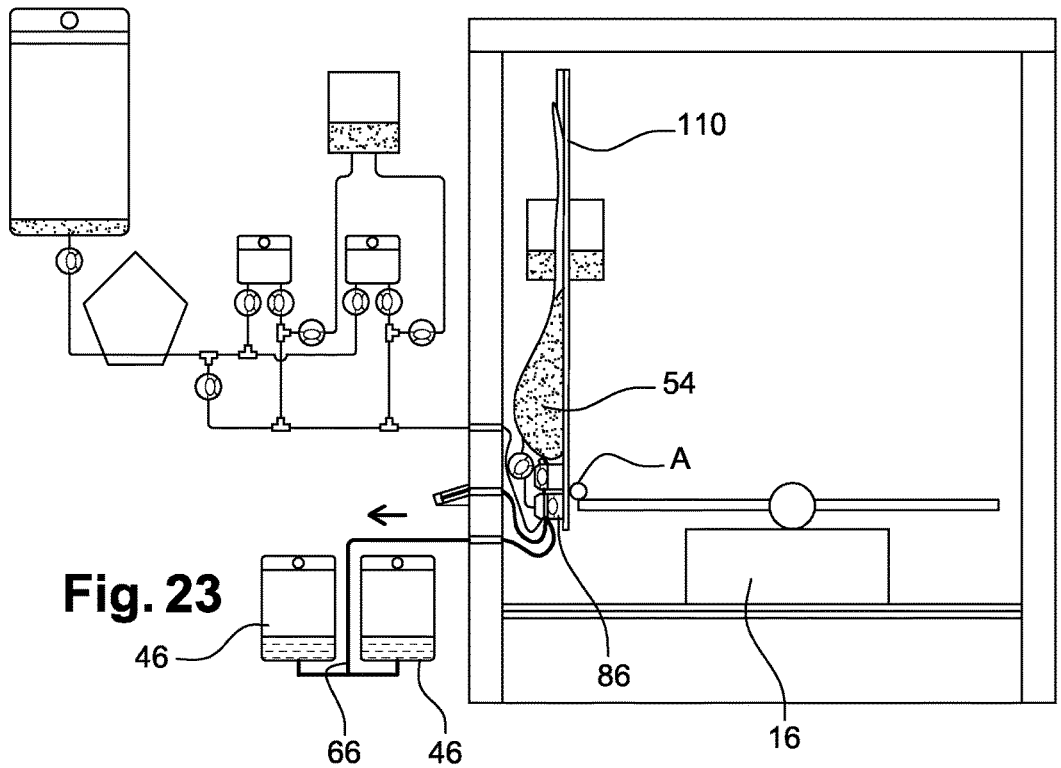
Figure 24:
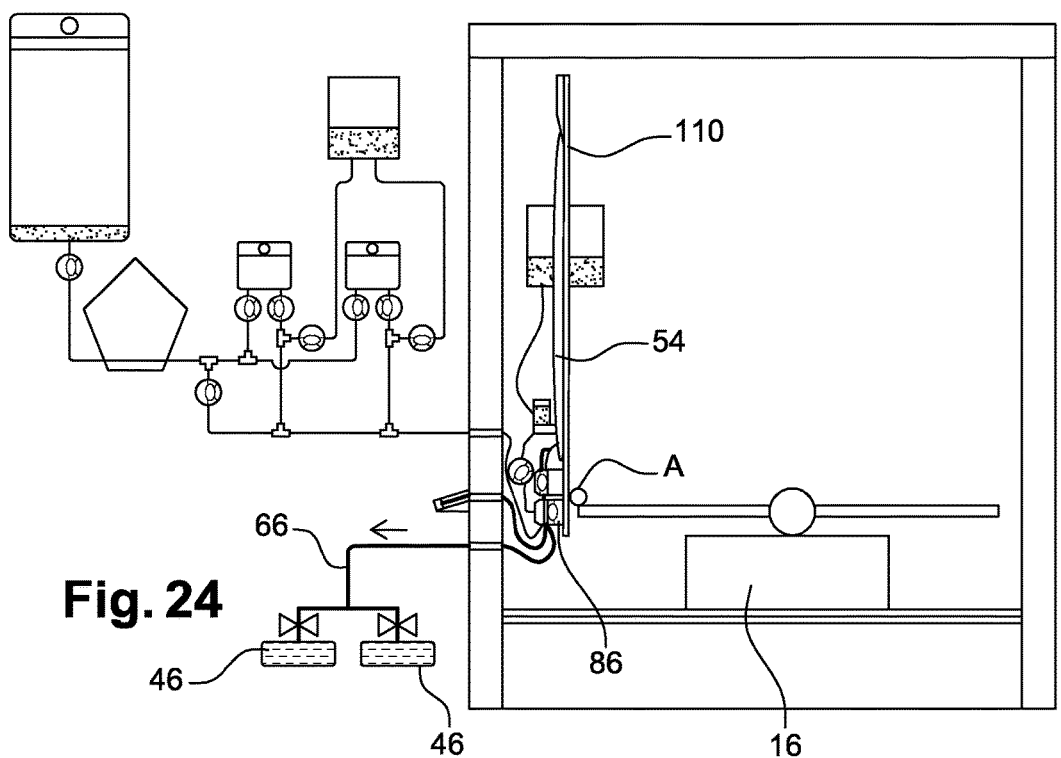

The method according to the invention further comprises a harvesting step 152 after cells culture (FIGS. 14, 23 and 24). At the end of the incubation step 144 and on request of the operator, the computer system 24 blocks the rotation of the tray 110 around the axis B and controls the jack 124 so that the tray 110 of the agitation device 16 moves around the axis A to a substantially vertical position shown in FIGS. 8, 23 and 24. The computer system 24 can then detect the correct position of the tray 110 via the sensors of the device 16.

The computer system 24 subsequently controls the opening of the valve 86 so that the contents of the cell expansion bag 54 flows by gravity into the two harvesting bags 46 through the tube 66 (FIG. 23).

The plates 42 carried by the frame 18 on which are hung the harvesting bags 46 may be displaced from their vertical position shown in FIGS. 2 and 23 to their horizontal position shown schematically in FIG. 24, either manually by the operator or by means of a displacement device controlled by the computer system 24. The tilting of the plates 46 allows the bags 46 to be located entirely below the bag 54 and at least a portion of the tube 66 so that the content of the cell expansion bag 54 is if possible fully transferred into the harvesting bags 46. When the operator has confirmed to the computer system 24 that the harvesting is completed, the system orders the closure of the valve 86 and the deployment of the jack so that the tray 110 returns to a substantially horizontal position.

The bags 46 are then removed from the automated apparatus 10 for possible treatment of the cells and the reinjection of these cells in the body of a patient for cell therapy, for example. For this, the tube 66 can be cut and welded by said clipper or the bags 46 are disconnected from the tube 66.

The last step of the method consists in a second phase of withdrawal 154 of consumables from the automated apparatus 10, the bags 54, 56 and the remaining tubes 66, 60, 70 and 78 being removed. For this, the computer system 24 controls the opening of the valves 86, 88, 90 and 92 to authorize the withdrawal by the operator of the tubes 66, 60, 70 and 78. Once the operator has confirmed the removal of these elements to the computer system 24, the latter controls the closing of the valves 86, 88, 90 and 92.

When the biological protocol is complete, the computer system can edit a culture report, this report may include the following information to ensure good traceability protocol: manufacturer-specific information (the identification number of the automate, operating system software version, biological monitoring protocol software version), the set of protocol parameters when at least one of these parameters is not the default, all culture parameters, the actions performed by the operator (including the date of each action yyyym-mddhhmimiss format, the author of this action via a connection identifier, the nature of the action via a coding to identify or an unambiguous wording "system" events (including the date of the event format yyyymmddhhmimiss, the nature of the event (alarm, user alert, failure detection, etc.) via a coding set or an unambiguous wording system, results of sample analysis (including the date of each sampling, the author of sampling, analytical results of sampling, etc.), and information of the graft (from the analysis of cells harvested after culture). This culture report can be accessed by the aforementioned network workstation.

The invention claimed is:

1. An automated apparatus of cell culture, comprising tanks of culture medium, growth factors and cells to be cultured, an incubator with a thermostated enclosure in which is housed a container for cell culture or expansion, and a control computer system including a mechanism configured for entering and recording data intended to control the culture conditions in the enclosure and to manage valves for dispensing fluids in a predefined sequence, wherein it comprises a device for supporting and agitating the cell culture or expansion container which is controlled by said computer system and which is housed in said enclosure, and wherein said container is formed by a cell expansion bag having at least one inlet port connected to said tanks and one outlet port connected to mechanisms configured for harvesting and storage of the cells after culture, these harvesting and storage mechanisms and said tanks being located outside the enclosure and being connected to said ports of said cell expansion bag by conduits which form with said cell expansion bag a preassembled module placed in said enclosure and which pass through a wall of said enclosure via a passageway means so as to allow to feed the cell expansion bag with said culture medium, growth factors and cells to be cultured, and to harvest the contents of said cell expansion bag in the mechanisms for harvesting and storage while maintaining the enclosure closed, and wherein the supporting and agitation device comprises a tray to support said cell expansion bag, which is mounted in rotation around a first horizontal axis and which is movable around said axis between a substantially horizontal position for cell culture and a substantially slightly vertical position for harvesting the cells after culture.

2. The automated apparatus according to claim 1, wherein said cell expansion bag further comprises a sampling outlet which is connected by a conduit to a sampling device located outside of said enclosure, said conduit passing through said wall of said incubator and being part of said preassembled module.

3. The automated apparatus according to claim 1, wherein said incubator includes a cabinet having an opening and equipped with a sealed closure door, means for the passageway of said conduits being mounted on the peripheral edge of said opening and having grooves which are slightly parallel and into which are engaged said conduits, said grooves being intended to be covered by said sealed closure door when in closed position.

4. The automated apparatus according to claim 1, wherein said tanks of growth factors and of cells to be cultured are formed by bags which are located above the inlet
port of said cell expansion bag, so that the content of each of the bags of growth factors and of cells to be cultured can flow by gravity to said cell expansion bag.

5. The automated apparatus according to claim 1, wherein said harvesting and storage means comprises one or two bags which are at least partially located below the outlet port of said cell expansion bag so that, after culturing, the content of said cell expansion bag can flow by gravity to said one or two bags of the harvesting and storage means.

6. The automated apparatus according to claim 1, wherein said cell expansion bag comprises flexible liquid-tight and gas permeable walls.

7. The automated apparatus according to claim 1, which comprises a peristaltic pump for controlling the supply of said culture medium to said cell expansion bag and to said tanks of growth factors and of cells to be cultured, for rinsing said tanks.

8. The automated apparatus according to claim 1, which comprises two bags forming air trap, one of which being connected to the tanks of growth factors and of cells to be cultured, and the other being connected to said cell expansion bag, said two bags being intended to collect and store the air contained in said conduits, said cell expansion bag and/or said tanks.

9. The automated apparatus according to claim 1, wherein said conduits are formed by flexible tubes, some of which going through valves which are intended in closed position, to pinch the tubes.

10. The automated apparatus according to claim 1, wherein the tray bears valves for controlling the supply of said cell expansion bag, the harvesting of the content of said cell expansion bag, and the sampling of said cell expansion bag.

11. The automated apparatus according to claim 1, wherein the supporting and agitation device comprises a vertical arm having at its upper end means for attaching a bag forming an air trap connected to said cell expansion bag.

12. The automated apparatus according to claim 1, wherein said mechanisms for harvesting and storage are mounted in rotation around a horizontal axis and are movable around said axis between a substantially vertical position and a substantially horizontal position in which said mechanisms for harvesting and storage are located completely below said cell expansion bag.

13. The automated apparatus according to claim 6, wherein said walls of said cell expansion bag have properties minimizing the adhesion thereto of said cells to be cultured.

14. A method, comprising the step of culturing stem cells of type CD34+ or blood mononuclear cells in the apparatus of claim 1.

15. The method of claim 14, comprising culturing lymphocytes.

16. The method according to claim 14, wherein the stem cells are issued from one or more sources.

17. The method according to claim 16, wherein the stem cells are issued from umbilical cord blood, bone marrow and/or whole blood.

18. An automated apparatus of cell culture, comprising:
tanks of culture medium,
growth factors and cells to be cultured,
an incubator with a thermostated enclosure in which is housed a container for cell culture or expansion,
a control computer system including a mechanism configured for entering and recording data intended to control the culture conditions in the enclosure and to manage valves for dispensing fluids in a predefined sequence, and
an agitation device for supporting and agitating the cell culture or expansion container, the agitation device disposed in said enclosure, and comprising a tray rotatably mounted about a first horizontal axis, the tray being moveable between a horizontal position to a vertical position, and wherein the agitation device is controlled by said computer system, and
wherein said container is formed by a cell expansion bag having at least one inlet port connected to said tanks and one outlet port connected to mechanisms configured for harvesting and storage of the cells after culture, these harvesting and storage mechanisms and said tanks being located outside the enclosure and being connected to said ports of said cell expansion bag by conduits which form with said cell expansion bag a preassembled module placed in said enclosure and which pass through a wall of said enclosure so as to allow to feed the cell expansion bag with said culture medium, growth factors and cells to be cultured, and to harvest the contents of said cell expansion bag in the harvesting and storage mechanisms while maintaining the enclosure closed, said tray being mounted in rotation around a second horizontal axis around which the tray is intended to oscillate for agitation and homogenization of the content of said cell expansion bag, said agitation device carrying a system for locking the rotation of the tray around the second axis.

19. An automated method of cell culture by means of an automated apparatu
according to one of claims 10 to 13, which comprises the steps of:

a) feeding said cell expansion bag with said culture medium, with said growth factors then with said cells to be cultured, while maintaining said enclosure of said incubator closed;

b) agitating said cell expansion bag in order to homogenize its content;

c) maintaining said cell expansion bag in incubation conditions for a predetermined period of time, and d) harvesting the content of said cell expansion bag in said harvesting and storage mechanisms while maintaining the enclosure closed.

20. The automated method of claim 19, which comprises:

prior to step a), a step of installing said preassembled module by fitting said cell expansion bag on said supporting and agitation device, by mounting said conduits in the passageway means of said incubator and into said valves, and by connecting said conduits to tanks or bags, and/or prior to step a), a step of evacuating air contained in said conduits by passage of culture medium from said culture medium tank to bags forming an air trap, and/or—after supplying said cell expansion bag with growth factors in step a), a step of rinsing said growth factors tank by flowing culture medium in said growth factors tank and then by draining its content to said cell expansion bag, and/or after supplying said cell expansion bag with cells to be cultured in step a), a step of rinsing the tank containing said cells to be cultured by flowing culture medium in said tank of cells to be cultured and then by draining its content to said cell expansion bag, and/or—during step c), one or more steps of sampling the contents of said cell expansion bag, which are each preceded by a step of tilting said tray from a horizontal position of cultivation to an inclined position in which a sampling outlet of said cell expansion bag is the lowest point of this bag and/or prior to step c), a step of removing the tanks of culture medium, of growth factors and of cells to be cultured by cutting and welding or pinching the conduit or tube connecting these tanks to the inlet port of said cell expansion bag, and/or before or during step d), a step of tilting said tray in a substantially vertical position so that the outlet port of said cell expansion bag represents the lowest point of this bag.

21. An automated apparatus according to claim 18, wherein said system for locking the rotation of the tray includes a retractable finger which cooperates with an element carried by a piece articulated on pivots fixed to the tray.

22. An automated apparatus according to claim 21, wherein said piece is a U-shaped part the free ends of the two lateral branches of which being articulated on said pivots fixed on side edges of the end of the tray.

23. An automated apparatus according to claim 18, wherein said first and second axis are parallel.

24. An automated apparatus according to claim 18, wherein the incubator comprises a cabinet having an interior space defining said thermostated enclosure, and wherein said agitation device is disposed in said interior space.

25. An automated apparatus according to claim 24, wherein the incubator comprises an opening which provides access to the interior space, and a door pivotably mounted on one side of the opening, the door configured to sealably close the opening.

26. An automated apparatus according to claim 18, wherein the incubator comprises a cabinet having an interior space defining said thermostated enclosure, and wherein said agitation device is disposed in said interior space.

* * * * *

UNITED STATES PATENT AND TRADEMARK OFFICE
CERTIFICATE OF CORRECTION

Page 1 of 1

PATENT NO. : 10,676,705 B2
APPLICATION NO. : 13/492356
DATED : June 9, 2020
INVENTOR(S) : Henon et al.

It is certified that error appears in the above-identified patent and that said Letters Patent is hereby corrected as shown below:

In the Claims

Column 17,
Lines 24 and 25, "means for the passageway" should read --the passageway means--;
Lines 37 and 41, both occurrences, "harvesting and storage means" should read --harvesting and storage mechanisms--.

Column 18,
Line 65, "automated apparatu" should read --automated apparatus--.

Signed and Sealed this
Twentieth Day of October, 2020

Andrei Iancu
*Director of the United States Patent and Trademark Office*